(12) United States Patent
McGregor et al.

(10) Patent No.: US 12,220,347 B2
(45) Date of Patent: Feb. 11, 2025

(54) CONVECTIVE WARMING DEVICE

(71) Applicant: Solventum Intellectual Properties Company, Maplewood, MN (US)

(72) Inventors: Andrew J. McGregor, West Lakeland, MN (US); John R. Stark, St. Paul, MN (US); James A. Thielen, Hugo, MN (US); Jenna L Lindsay, Woodbury, MN (US); Daniel P. Doran, Minneapolis, MN (US); Amanda M. Rue, St. Paul, MN (US); Benjamin C. Stanaway, St. Paul, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 550 days.

(21) Appl. No.: 17/621,401

(22) PCT Filed: Jun. 26, 2020

(86) PCT No.: PCT/IB2020/056078
§ 371 (c)(1),
(2) Date: Dec. 21, 2021

(87) PCT Pub. No.: WO2020/261212
PCT Pub. Date: Dec. 30, 2020

(65) Prior Publication Data
US 2022/0354688 A1 Nov. 10, 2022

Related U.S. Application Data

(60) Provisional application No. 62/866,690, filed on Jun. 26, 2019.

(51) Int. Cl.
*A61F 7/00* (2006.01)
*A61F 7/02* (2006.01)

(52) U.S. Cl.
CPC .............. *A61F 7/0097* (2013.01); *A61F 7/02* (2013.01); *A61F 2007/006* (2013.01); *A61F 2007/0091* (2013.01); *A61F 2007/0234* (2013.01)

(58) Field of Classification Search
CPC ..................................................... A61F 7/0097
See application file for complete search history.

(56) References Cited

U.S. PATENT DOCUMENTS 4,118,531 A 10/1978 Hauser
4,867,230 A * 9/1989 Voss ...................... A61F 7/0097
607/104

(Continued)

FOREIGN PATENT DOCUMENTS

CN 206964075 2/2018
EP 0389561 10/1995

(Continued)

OTHER PUBLICATIONS

3M, "Technical Data Sheet Typical Values", 3M (TM) Thinsulate (TM) Insulation (Types U/US/UDS) Product Designation Basis Weight, Aug. 1, 2016, 4 pages, XP055729766.

(Continued)

*Primary Examiner* — Kaitlyn E Smith
(74) *Attorney, Agent, or Firm* — Vorys, Sater, Seymour and Pease LLP

(57) ABSTRACT

Aspects of the present disclosure relate to a warming system including a warming device. The warming device includes a clinical garment comprising a body portion adapted to cover a portion of a patient, an inner surface for facing the patient, and an outer surface for facing away from the patient. The body portion includes sleeves sized and positioned for receiving the patient's arms and a torso portion adapted to cover an anterior torso of a patient. A first pneumatic convective device can be disposed adjacent to the inner (Continued)

surface of the clinical garment. The pneumatic convective device can include an opening formed in the clinical garment for admitting a stream of pressurized, warmed air into the first pneumatic convective device. The warming system can also have a second pneumatic convective device in a fully-folded configuration or partially-folded configuration and disposed on a portion of the clinical garment.

19 Claims, 19 Drawing Sheets

(56) References Cited

U.S. PATENT DOCUMENTS

| | | | |
|---|---|---|---|
| 5,148,002 | A | 9/1992 | Kuo |
| 5,891,187 | A | 4/1999 | Winthrop |
| 5,997,572 | A | 12/1999 | Arnold |
| 6,245,096 | B1 * | 6/2001 | Tomic-Edgar ............ A61F 7/00 607/104 |
| 7,862,599 | B2 | 1/2011 | Anderson |
| 2004/0040087 | A1 | 3/2004 | Lack |
| 2006/0247745 | A1 | 11/2006 | Thompson |
| 2012/0047623 | A1 | 3/2012 | Van Oudenallen |
| 2012/0305541 | A1 | 12/2012 | Giles |
| 2014/0058485 | A1 | 2/2014 | Augustine |
| 2015/0374048 | A1 | 12/2015 | Theodossiou |
| 2019/0110615 | A1 | 4/2019 | Vergona |

FOREIGN PATENT DOCUMENTS

| | | |
|---|---|---|
| EP | 1937196 | 2/2013 |
| EP | 2611399 | 7/2015 |
| JP | 2017-141517 | 8/2017 |
| WO | WO 2001-017470 | 3/2001 |
| WO | WO 2006-076148 | 7/2006 |
| WO | WO 2006-086587 | 8/2006 |
| WO | WO 2007-047917 | 4/2007 |
| WO | WO 2011-049744 | 4/2011 |
| WO | WO 2014-092874 | 6/2014 |
| WO | WO 2014-180975 | 11/2014 |
| WO | WO 2016-105461 | 6/2016 |
| WO | WO 2016-105462 | 6/2016 |
| WO | WO 2016-105475 | 6/2016 |
| WO | WO 2020-261186 | 12/2020 |
| WO | WO 2020-261211 | 12/2020 |

OTHER PUBLICATIONS

Fanger, "Thermal Comfort: Analysis and Applications in Environmental Engineering", Danish Technical Press, 1970, pp. 5-67.
International Search Report for PCT Application No. PCT/IB2020/056040, mailed on Sep. 17, 2020, 7 pages.
International Search Report for PCT Application No. PCT/IB2020/056077, mailed on Sep. 23, 2020, 8 pages.
International Search Report for PCT Application No. PCT/IB2020/056078, mailed on Sep. 23, 2020, 8 pages.

* cited by examiner

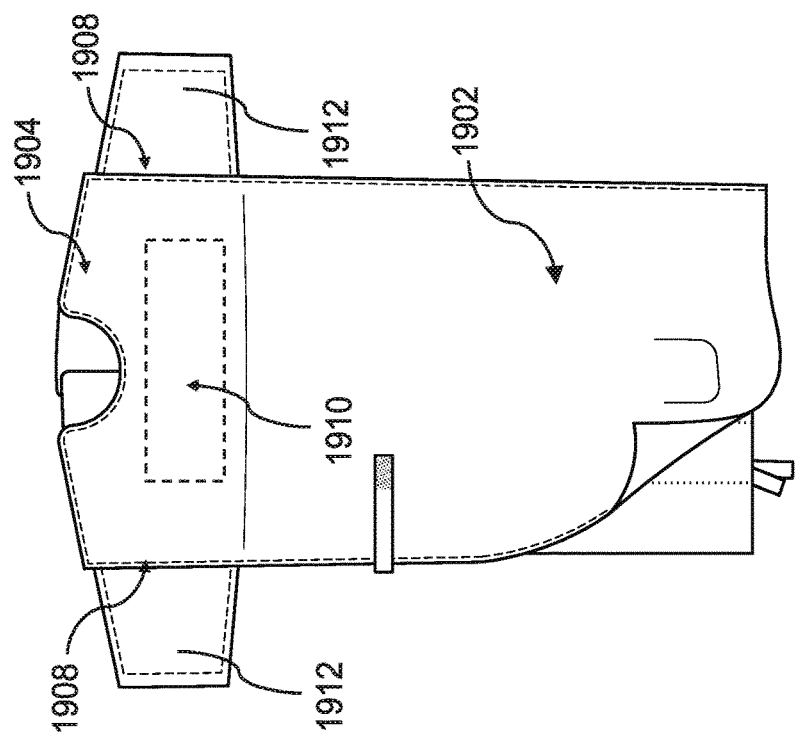
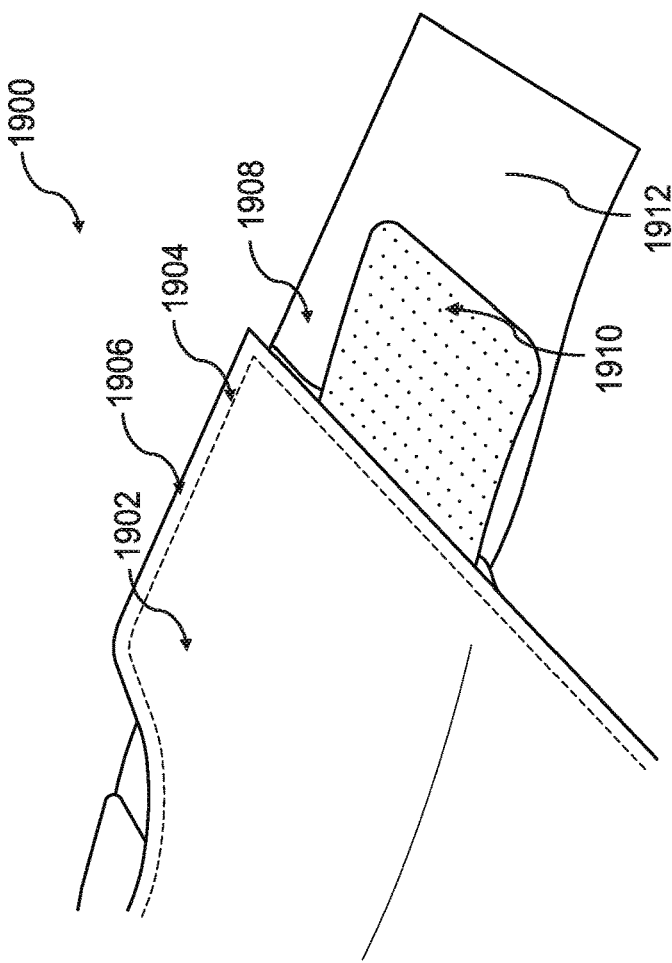
FIG. 19A
FIG. 19B

CONVECTIVE WARMING DEVICE

CROSS REFERENCE TO RELATED APPLICATIONS

This application is a national stage filing under 35 U.S.C. 371 of PCT/IB2020/056078, filed Jun. 26, 2020, which claims the benefit of U.S. Provisional Patent Application No. 62/866,690, filed Jun. 26, 2019, the disclosures of which are incorporated by reference in their entirety herein.

BACKGROUND

Pneumatic devices which transfer heat between thermally-conditioned air and a body are known. For example, there are inflatable pneumatic devices that receive a stream of pressurized, warmed air, inflate in response to the pressurized air, distribute the warmed air within a pneumatic structure, and emit the warmed air onto a body to accomplish such objectives as increasing comfort, reducing shivering, and treating or preventing hypothermia. These inflatable devices are typically characterized as "blankets" or "covers". 3M makes and sells such devices under the BAIR HUGGER trade designation. One such device is the Model 622 Blanket.

Inflatable pneumatic warming blanket or cover devices are adapted especially for use with supine persons and are typically deployed by being laid directly on a person lying on a bed, a gurney, or a surgery platform, so as to drape over or cover some portion of the person. Because these devices are designed to cover and hang about or over a supine person, they are not easily or readily deployed on persons who are standing, sitting, reclining or moving. In particular, inflatable blankets are not suitable in a clinical setting in which it is desirable to warm a patient, and also necessary that the patient be able to move about and between various postures. In addition, there are a variety of clinical settings in which patient warming is desirable, with each setting requiring its own unique access to patient anatomy that may not be afforded by an inflatable blanket. For example, examination or treatment of a patient in a post anesthesia care unit (PACU) could call for access to patient lines in the chest area, setting IV's in the arm, application of a stethoscope to the back and/or side, or application of a blood pressure cuff. Further, patient mobility throughout a clinic, nursing home, hospice care, or a hospital is highly desirable, but would be severely curtailed with use of inflatable blankets. For example, transporting a patient to an x-ray or MRI location in a wheelchair, would be made problematic with an inflatable blanket.

Gowns including pneumatic convective devices are also known and provide warmth to patients in a perioperative environment. For example, convective gowns can be used in a preoperative setting, i.e., before surgery and typically while waiting in a different room from the operating room, as comfort warming or in a ward. Such gowns are not necessarily designed for prewarming, which can be useful in preventing anesthesia-related hypothermia.

SUMMARY

Warming devices can be used in a preoperative period and a separate pneumatic convective device can be used in the operative period. This can result in waste of clinician time as some can be searching for the separate pneumatic convective devices during the operative period. By having a warming device and a pneumatic convective device packaged together as system, comfort and therapeutic warming can both be facilitated without loss of clinician resources or attention.

Aspects of the present disclosure relate to a warming system including a warming device. The warming device includes a clinical garment comprising a body portion adapted to cover a portion of a patient, an inner surface for facing the patient, and an outer surface for facing away from the patient. The body portion includes sleeves sized and positioned for receiving the patient's arms and a torso portion adapted to cover an anterior torso of a patient. A first pneumatic convective device can be disposed adjacent to the inner surface of the clinical garment. The pneumatic convective device can include an opening formed in the clinical garment for admitting a stream of pressurized, warmed air into the first pneumatic convective device. The warming system can also have a second pneumatic convective device in a fully-folded configuration or partially-folded configuration and disposed on a portion of the clinical garment.

Additional aspects of the present disclosure relate to warming the patient.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

FIGS. 19A-B illustrate a warming system 1900 in accordance with one embodiment.

DETAILED DESCRIPTION

"Clinical garment" refers to a garment that is typically used to temporarily clothe a person in a clinical setting while awaiting and undergoing treatment. Clinical garments include hospital gowns, robes, bibs, and other equivalents. The clinical setting may be a medical, dental, or veterinary office or clinic, a hospital, or any facility or institution that provides treatment to patients.

"Fully-folded configuration" refers to at least three folds. The surface area of one face is no greater than 20% of the total surface area of the pneumatic convective device.

"Patient" refers to a human undergoing a surgical procedure. Dimensions of the patient are established by the median value of a statistically relevant number of patients.

"Width dimension" refers to a dimension measured perpendicular from an axis of a particular body. For example, a width dimension of a pocket refers to the measurement along an axis which is perpendicular to the pocket axis. A width dimension of a gown refers to the measurement along an axis that is perpendicular to the longitudinal axis.

"Length dimension" refers to a dimension measured parallel to a longitudinal axis of a particular body. For example, a length dimension of a pocket refers to the measurement along the pocket axis. A length dimension of a gown refers to the measurement along the longitudinal axis.

"Fastening device" refers to a device or technique that fastens two sheets together.

"Recloseable fastener" refers to a type of fastening device to allow repositioning of an article from a first application surface to a second application surface without damaging either the article or the first or second application surface.

"Fixed fastener" refers to a fastening device that will damage the underlying material if separated.

Aspects of the present disclosure relate to a warming system comprising a warming device. The warming device includes a clinical garment and a pocket disposed or formed thereon or therein. The pocket is dimensioned to receive a pneumatic convective device such as a patient warming blanket that can be accessed by a clinician.

Figure 1:
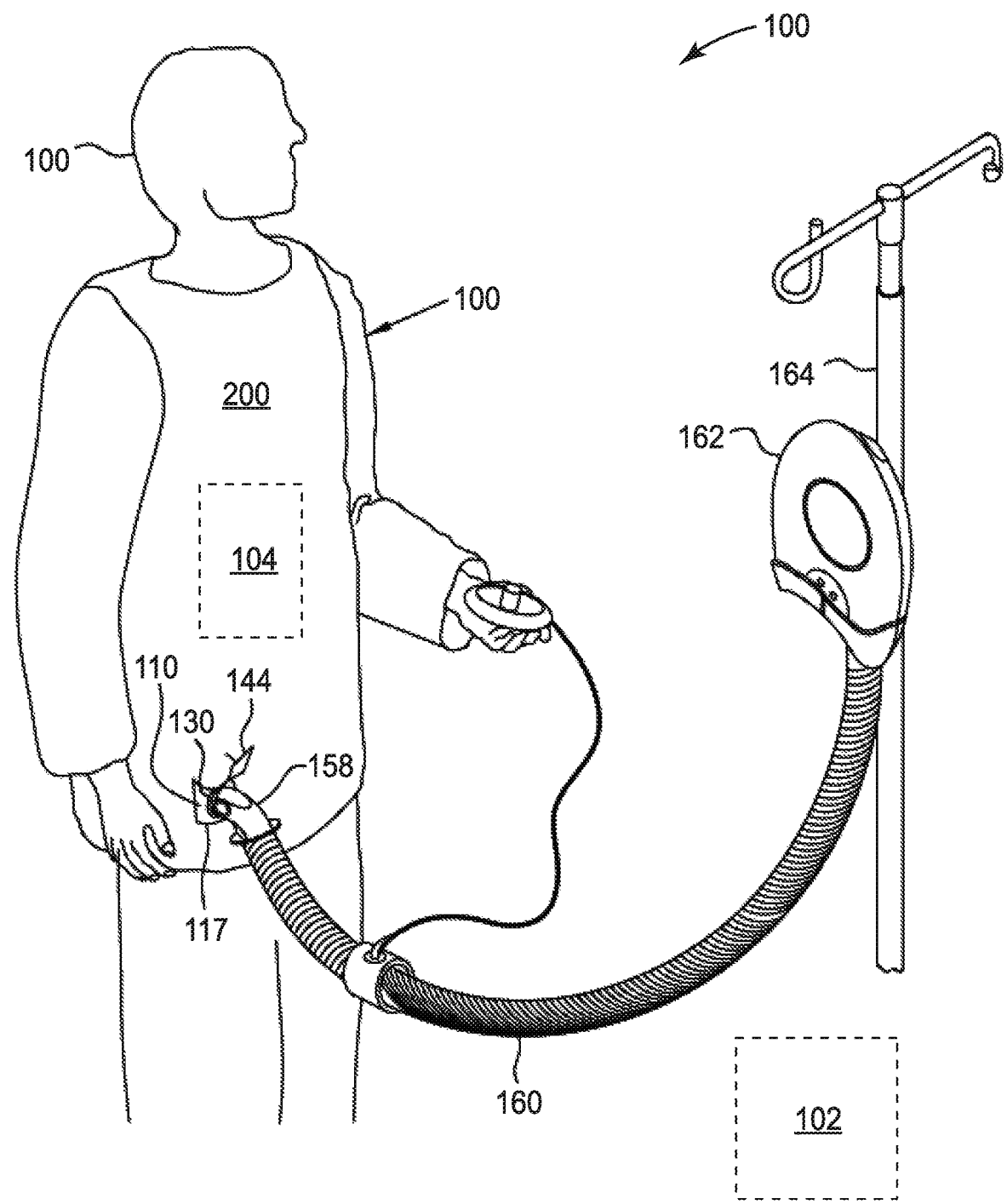
FIG. 1 illustrates a warming system 100 in accordance with one embodiment.

FIG. 1 illustrates a warming system 100 comprising a patient 108 (shown in the standing position) wearing a warming system 200 comprising a clinical garment 112 and a plurality of pneumatic convective devices (e.g., 110). The warming system 100 can also include a pocket 104 as described further herein.

The patient 108 may be in a doctor's office in an outpatient facility, or any other suitable location. The clinical garment 112 is shown with connecting lines that illustrate how it would be attached to the patient 108. While various sizes of patients can exist, patient can preferably mean a statistically average adult human male. An end 158 of an air hose 160 is connected to the pneumatic convective device 110 may be received with the hose card 130 to provide a stream of pressurized, thermally treated air directed into the device 110 through inlet port 117. A flap 144 can extend off of a portion of the clinical garment 112 that, when the flap 144 is lifted, the inlet port 127 and the hose card 130 as exposed, through an opening. Access to the hose card 130 can also be on the front of the clinical garment 112 if there is no gown opening. The other end of the air hose 160 is connected to a warming unit 162 that can provide a stream of pressurized, thermally controlled air to the device. Warming units and components can be commercially available as model 675, model 775, or model 875 under the trade designation Bair Hugger. A second pneumatic convective device 102 can be present which is associated with the warming system 200 and removed before or during a preoperative procedure as described herein.

In at least one embodiment, the second pneumatic convective device 102 can be contained in a sealed package. A sealed package can be a covering that contains the second pneumatic convective device 102. In at least one embodiment, the sealed package can be a plastic packaging. The entire sealed package can be releasably attached to the clinical garment 112.

The clinical garment 112 can be configured similar to the commercially available Bair Hugger Warming Gown except with a pocket dimensioned to receive a recloseable fastener pneumatic convective device. The clinical garment 112 can be associated with a first pneumatic convective device that is not recloseable fastener (meaning cannot be removed without causing irreparable damage to the clinical garment 112) as found in patient warming gowns. The first pneumatic convective device can be a contained bladder separate from the clinical garment as found in the Bair Hugger Warming Gown or the first pneumatic convective device can be formed with a portion of the clinical garment 112 and an air permeable sheet. The recloseable fastener pneumatic convective device can be commercially available under the trade designation Bair Hugger and examples include a multi-position upper body warming blanket (model 622).

In at least one embodiment, the clinical garment can be made from a woven cloth, such as cotton, or a non-woven such as spunbond-meltblown-spunbond material (SMS), and the seals between the portion of its inside surface 152 and an optional extruded layer of a laminate sheet may be formed by a gluing, a heating, or an ultrasonic process. Examples of non-woven material include any one or more of polyester, cotton, rayon, polypropylene, and wood pulp. Examples of extruded synthetic material include polypropylene, polyesters, and polyurethanes. In at least one embodiment, the clinical garment can be treated with a material to make a portion of the clinical garment air impermeable. In at least one embodiment, the clinical garment 112 is a disposable gown that is configured to be single-use by a patient before the clinical garment 112 is disposed as medical waste.

The clinical garment described in the above and in below-described embodiments may be a standard gown, a modified gown or a special purpose gown. The gowns may have rear openings, front openings or other openings suitable openings, such as a head opening in a poncho type gown. One type of gown shown in the figures has a rear opening which is configured to open in the rear of a patient.

Figure 2:
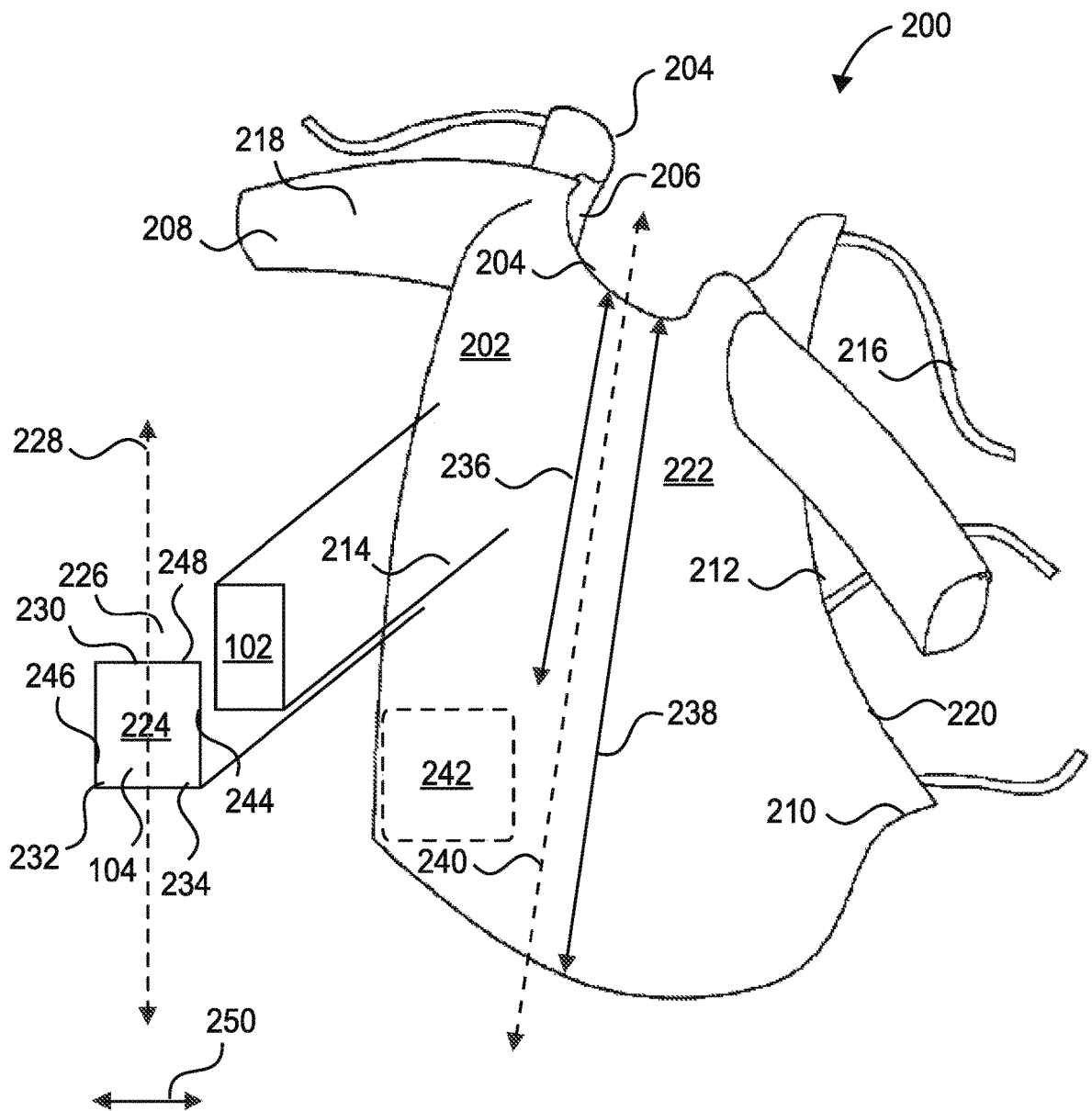
FIG. 2 illustrates a warming system 200 in accordance with one embodiment.

FIG. 2 illustrates warming system 200. The warming system 200 comprises a warming device comprising a clinical garment 202 having a pocket 104 disposed on at least a portion thereon. In at least one embodiment, the clinical garment 202 can have an insulative material disposed thereon. As used herein, the term warming device can include any clinical garment and associated device such as a fixedly attached pneumatic convective device but generally not a removable pneumatic convective device.

An insulative clinical garment 202 can be particularly advantageous in situations where a pneumatic convective device and the associated warming unit may not be practical. In at least one embodiment, the insulative material can have a surface area that is at least 50%, at least 60%, at least 70%, at least 80%, at least 90% of the total surface area (e.g., inner or outer surface 218, body and sleeves 208) of the clinical garment 202.

In at least one embodiment, the clinical garment 202 can be structured similarly to the clinical garment 112 as described herein except without the openings. The clinical garment 202 can have body portion 222 and sleeves 208. The body portion 222 can have outer surface 218.

The clinical garment 202 can have a neck opening 204 and a hemline 210. The clinical garment 202 can have at least one opening into the clinical garment 202. For example, a rear slit 212 through the clinical garment 202 can create an opening for a patient to easily remove the clinical garment 202. Fastening devices 216 can fasten opposing ends of the rear slit 212 together to provide for ease in securing the clinical garment 112 to the patient as well as allowing for ease in adjusting the size of the clinical garment to accommodate various different size wearers. For example, snap buttons or hook-and-loop positioned along opposing sides of the rear slit 212 that can be brought together and fastened to hold the clinical garment 112 to the patient. Another method attachment shown is a plurality of strings positioned along opposing sides of the rear slit 212 that can be tied together for hold the clinical garment 112 to the patient. Other fastening devices 216 described herein can include fixed fastener or fixed methods such as ultrasonic or thermal welding, adhesive, or recloseable fastener or releasable methods such as snaps, repositionable adhesive, hook and loop elements, double-sided adhesive, snaps, rivets, and any and all equivalents thereof.

In at least one embodiment, the body portion 222 can be separated into a torso portion 214 that aligns with a patient's torso, in particular the anterior torso of the patient. The torso portion 214 can be established by a traverse plane of the patient and can vary depending on the patient. The dimension 236 from the neck opening 204 to the traverse plane of the patient can be no greater than 32 inches, no greater than 30 inches, or no greater than 28 inches. The dimension 238 from the neck opening 204 to the hemline 210 (along a longitudinal axis 240 from a nadir of the neck opening 204) can be from 30 inches to 56 inches. Preferably, the dimension 238 can be from 40 to 46 inches.

In at least one embodiment, the body portion 222 can further be divided into one or more regions. For example, the body portion 222 can be intersected by line which can divide the body portion 222 into the torso portion 214 and the leg portion. The line can align with the transverse plane, or axial plane of a patient. For example, the torso portion 214 can correspond to the superior part of the patient and the leg portion can correspond to the inferior part of the patient.

The sleeves 208 can have a diameter. In at least one embodiment, the diameter can vary from the armhole end near the torso portion 214 vs the cuff end near the hands of the patient. In at least one embodiment, the diameter can be 6-15 inches, 8-15 inches, 10-15 inches, or 10-14 inches near the cuff end.

In at least one embodiment, the clinical garment 202 can include a pocket 104 dimensioned to receive pneumatic convective device 102 (which is recloseable fastener). The pneumatic convective device 102 can be in a fully-folded configuration or a partially-folded configuration as described further herein.

In at least one embodiment, the pocket 104 can be formed from a sheet of material 224 and the outer surface 218. The sheet of material 224 is formed from a sheet of material that can be the same as the clinical garment 202. Sheet of material 224 can be attached to the clinical garment 202 anywhere on the body portion 222 (e.g., region 242) but preferably on the torso portion 214, and most preferably on the front portion (defined by the chest of the patient). In at least one embodiment, the sheet of material 224 can be within 10 inches of any portion of the neck opening 204. Alternatively, the pocket 104 can be placed on an inner surface 206 of the clinical garment 202 as described further herein.

The sheet of material 224 can be attached via an adhesive or stitching along any portion of the pocket sheet perimeter 234, including along at least a portion or even the entire pocket sheet perimeter 234.

In at least one embodiment, the sheet of material 224 is attached with a fastening device to the clinical garment 202 adjacent to or at the sheet edge 246 and sheet edge 244 and the sheet edge 232. The sheet edge 230 can be unattached to form a pocket opening 248. In at least one embodiment, the pocket opening 248 can be dimensioned to remove the pneumatic convective device 102 without damaging the fastening device between clinical garment 202 and sheet edge 246, sheet edge 244, or sheet edge 232. In one example, the unattached portion of the sheet edge 230 can be at least 60 percent, at least 70, at least 80, or at least 90 percent of a width dimension 250 (which is perpendicular to the pocket axis 228) of the sheet of material 224. In at least one embodiment, the width dimension 250 can be between 4 and 15 inches.

The sheet of material 224 can also be attached to the clinical garment 202 along the sheet edge 230, sheet edge 232, and sheet edge 244 (e.g., along two length dimensions and one width dimension) and unattached to the clinical garment 202 at sheet edge 246. Although not shown, the sheet of material 224 can have an indented region. In at least one embodiment, the sheet of material can be a pneumatic convective device as described further herein.

The sheet of material 224 can have a sheet edge 230 and sheet edge 232 that are opposing and oriented along the pocket axis 228. The pocket axis 228 can be established by the pocket opening 248. In at least one embodiment, the angle formed between the pocket axis 228 and longitudinal axis 240 is no greater than 90 degrees (i.e., oriented vertically).

The distance from sheet edge 230 to sheet edge 232 (e.g., a length dimension) can be larger than that of the distance between sheet edge 246 and sheet edge 244 (e.g., a width dimension 250) of the sheet of material 224. In at least one embodiment, the sheet of material 224 can have a line of weakness such as a perforation, a physically weaken area that is configured to break upon an applied force. For example, the sheet of material 224 can form a pocket cavity 226 which can support, contain, or even entomb the pneumatic convective device 102 on the outer surface 218. A user can break the line of weakness of the sheet edge 232 to extract the pneumatic convective device 102 from pocket cavity 226.

In at least one embodiment, the pocket 104 can be an internal pocket, i.e., with pocket cavity 226 disposed proximate the inner surface 206. In at least one embodiment, the internal pocket can have an exterior opening to access the pneumatic convective device 102.

Figure 3:
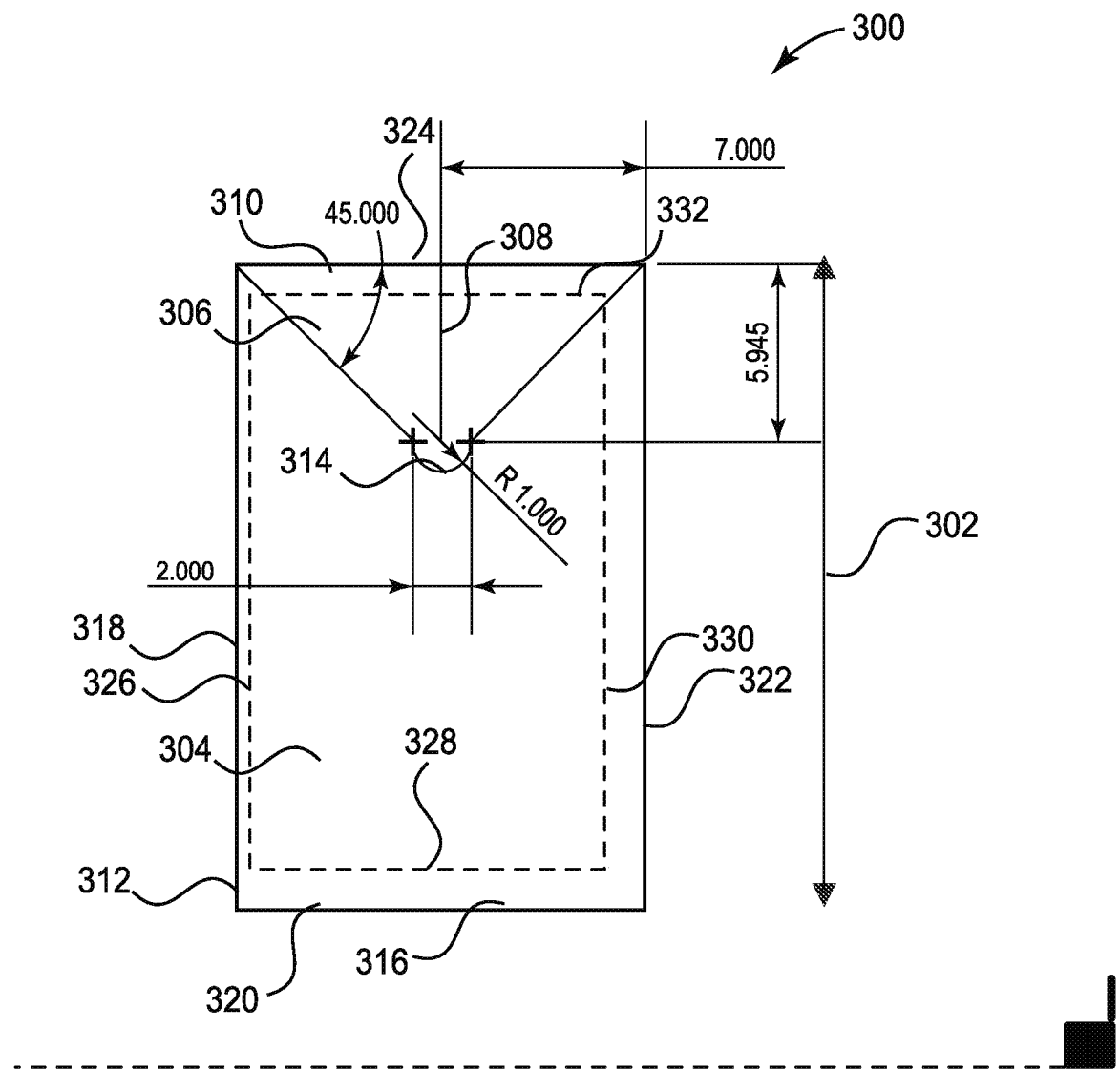
FIG. 3 illustrates a pocket 300 in accordance with one embodiment.

FIG. 3 illustrates an example of a pocket 300. The pocket 300 can be envelope-shaped. For example, the pocket 300 can have a flap portion 306 and a sheet of material 304. The flap portion 306 can overlap a portion of the sheet of material 304 sufficient to secure a pneumatic convective device contained in the pocket cavity therein.

In at least one embodiment, the flap portion 306 can include a tip 314 that can engage with a face of the sheet of material 304. As shown the flap portion 306 is triangular with a minor vertex being approximately 45 degrees. The dimension 308 can be from the tip 314 to the flap end 310 along a pocket axis. Example dimensions for dimension 308 can be between 4 and 8 inches or 5 to 7 inches.

The pocket 300 can also include a dimension 302 from the flap end 310 to the end 316. The pocket 300 can also have a perimeter 312 that is established by both the flap portion 306 at flap end 310 and the sealed portions of sheet of material 304.

In at least one embodiment, the perimeter 312 can include sheet edge 318, sheet edge 320, sheet edge 322, and flap edge 324. One or more seals (either continuous or non-continuous) can bind the sheet of material 304 or flap portion 306 to the clinical garment. The fastened regions can be formed using any fastening device but is preferably non-removable or permanent fastening device such as ultrasonic welding, or adhesive. The seals can be adjacent to the edge meaning within 1 cm. As shown, fastened region 326, fastened region 328, fastened region 330 can seal the sheet of material 304 to the clinical garment, leaving an unsealed section proximate flap end 310 to form a pocket opening. The fastened region 332 can secure a portion of the flap portion 306.

Figure 4:
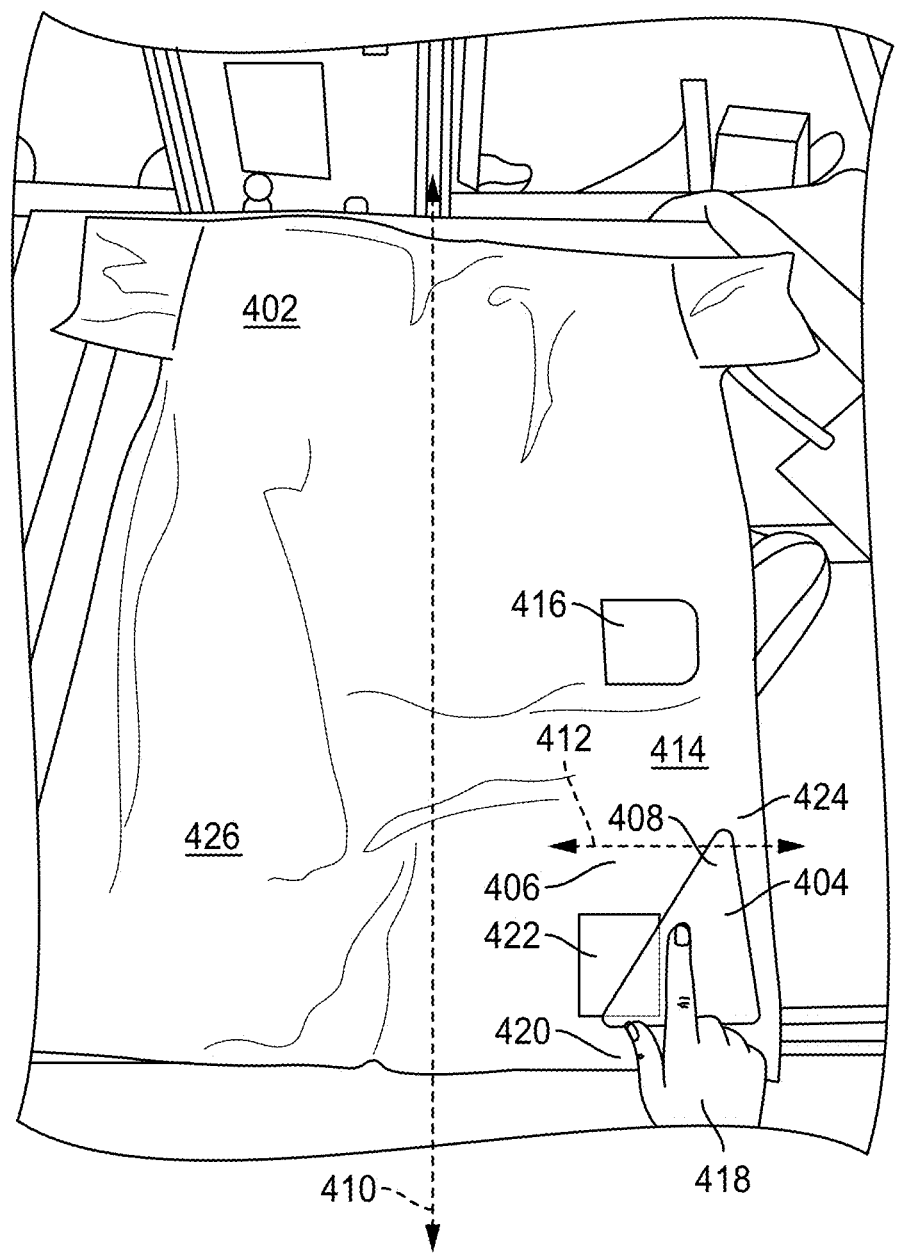
FIG. 4 illustrates a warming system 400 with a pocket in a first configuration in accordance with one embodiment.
Figure 5:
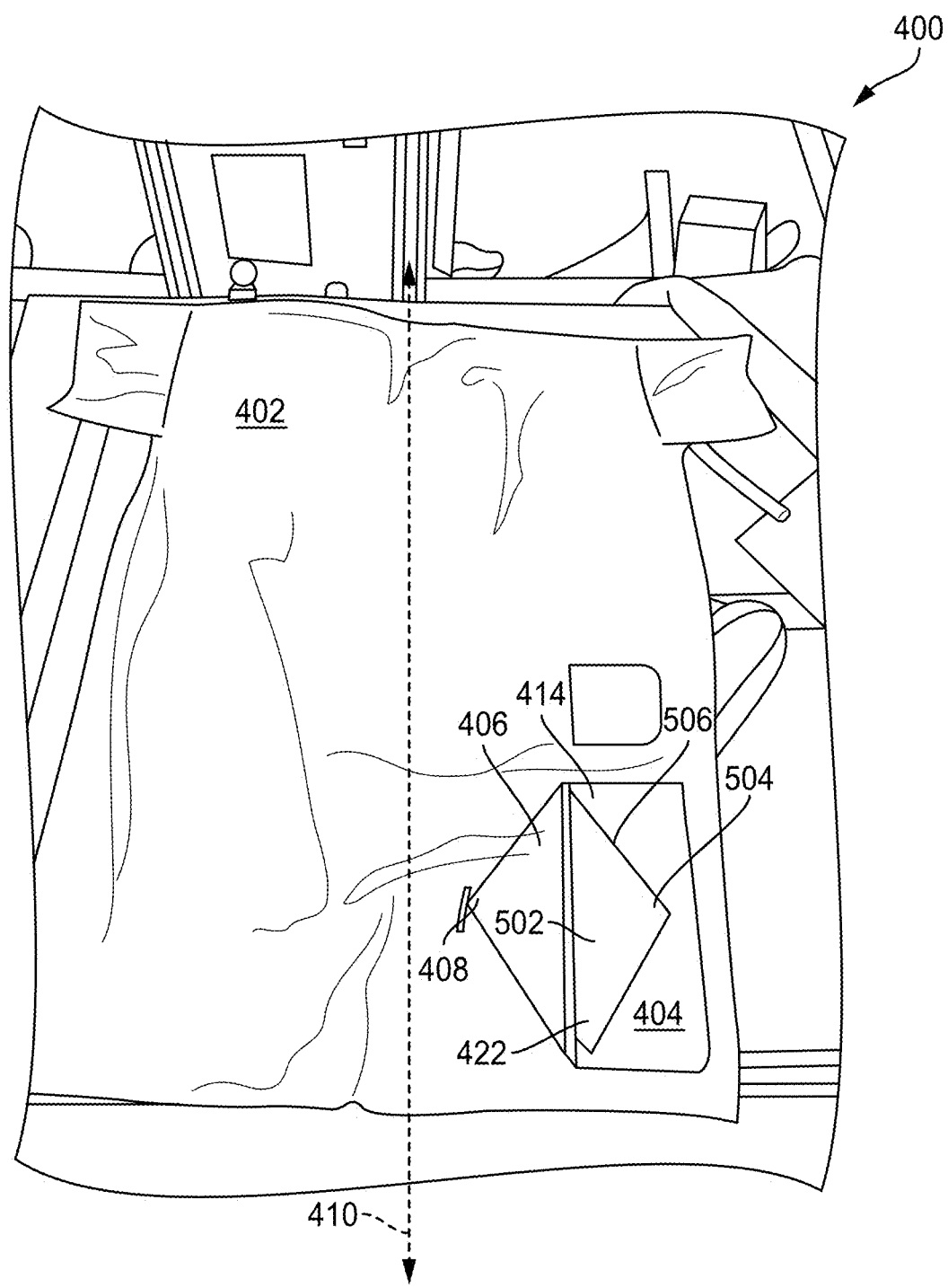
FIG. 5 illustrates the warming system 400 with the pocket in a second configuration in accordance with one embodiment.
Figure 6:
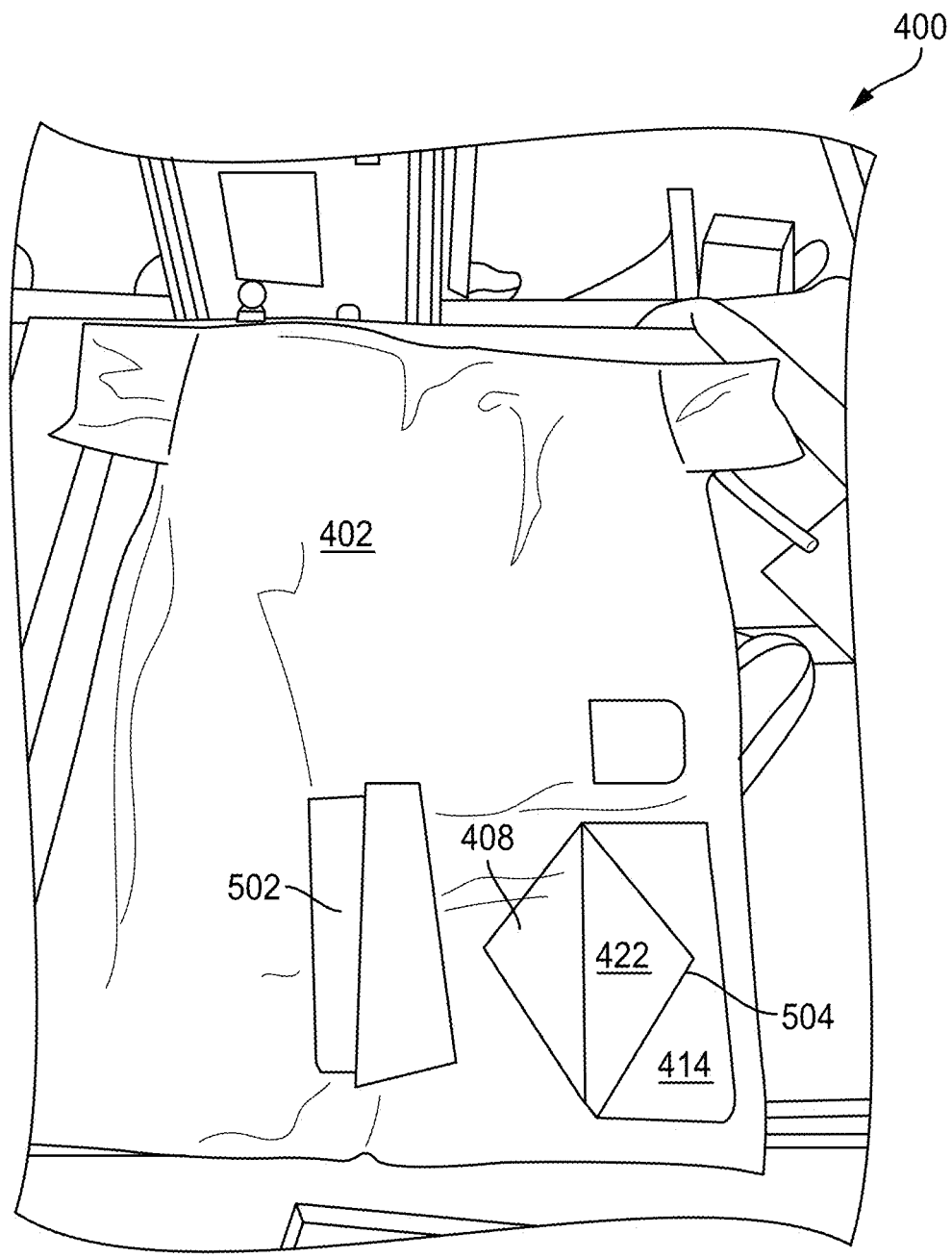
FIG. 6 illustrates the warming system 400 with a pneumatic convective device removed from the pocket in accordance with one embodiment.
Figure 7:
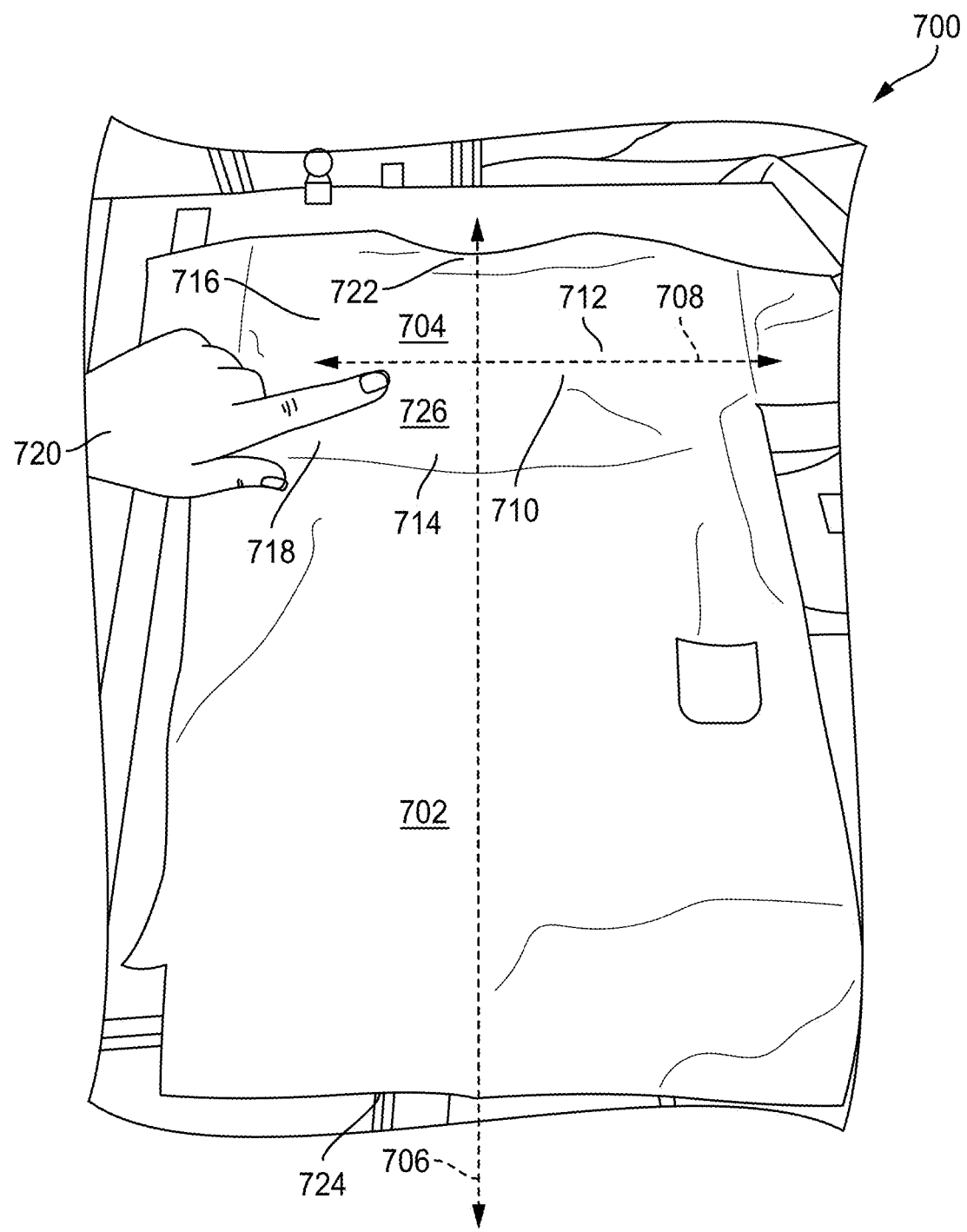
FIG. 7 illustrates a warming system 700 with a pocket in a first configuration in accordance with one embodiment.

FIG. 4-FIG. 6 show a warming system 400 that includes a clinical garment 402 and a pneumatic convective device 502.

As shown in FIG. 4, a clinician 418 can access the pneumatic convective device on the inner surface at cover flap 416. The warming system 400 can have a longitudinal axis 410 oriented lengthwise along a major medial axis of the clinical garment 402.

In at least one embodiment, the clinical garment 402 also includes a pocket 414 positioned below the transverse plane (toward the legs) of a patient. The pocket 414 is outside of the cover flap 416 leading to a pneumatic convective device. In at least one embodiment, portions of the pocket 414 are mounted to the outer surface 426 as described herein. The pocket 414 is dimensioned and configured to hold a recloseable fastener pneumatic convective device in a fully-folded configuration or a partially-folded configuration. In at least one embodiment, a pocket opening can be distinguished from a hand opening as can be found in hoodie-type pockets in that the pocket opening (formed from two sheets) has a circumference of at least 15 inches, at least 18 inches, at least 20 inches, at least 22 inches, or at least 26 inches. At least one side can be openable. In at least one embodiment, the pocket 414 can have dimensions between 17 and 340 cubic inches. The pocket 414 can also have a surface area between 35 and 170 square inches. The thickness of the pocket 414 (when full) can be no greater than 2 inches, no greater than 1 inch, no greater than 0.5 inch, or no greater than 0.3 inches. The length dimension can be from 7 to 17 inches. The width dimension can be from 5 to 10 inches.

The pocket 414 can include a sheet of material 404 and a flap portion 406. The sheet of material 404 can be a sheet with an indented region configured to facilitate removal of the enclosed pneumatic convective device. The indented region and the fastened regions can define a pocket cavity 422 in which a pneumatic convective device is inserted. The sheet of material 404 can be fastened to the clinical garment 402 via a fastening device to form the fastened region adjacent to the perimeter 420. The width dimensions and a length dimension can be fastened, and the indented region can be unfastened.

In at least one embodiment, the flap portion 406 can include a tip 408. The flap portion 406 can be fastened to the clinical garment 402 along a width dimension such that the tip 408 moves freely. A pocket axis 412 can be oriented along the pocket cavity 422 such that the opening direction is established by the pocket axis 412. The tip 408 and a pocket nadir 424 of the pocket 414 can form the pocket axis 412. In at least one embodiment, the pocket axis 412 and longitudinal axis 410 form an angle no greater than 90 degrees.

FIG. 5 illustrates the warming system 400 with the pocket 414 in an open position. The flap portion 406 can be extended so that the tip 408 is moved in the direction of the pocket axis to expose a pocket opening 506 formed by the sheet of material 404 and clinical garment 402 that leads to a pocket cavity 422 formed by the sheet of material 404. The pneumatic convective device 502 is shown in a fully-folded configuration and placed in the pocket cavity 422. The indented region 504 can facilitate the removal of the pneumatic convective device 502.

FIG. 6 illustrates the warming system 400 with the pneumatic convective device 502 removed from the pocket cavity 422. In use, a clinician 418 can first lift tip 408 from indented region 504. In at least one embodiment, the tip 408 can be attached to indented region 504 via an adhesive. After the tip 408 is lifted, then the pneumatic convective device 502 is exposed. A clinician can grab and remove the pneumatic convective device 502 from pocket cavity 422. Optionally, a portion of the pneumatic convective device 502 can be attached to the clinical garment 402 with a recloseable fastener fastening device.

FIG. 7-FIG. 11 illustrate an embodiment of a warming system 700. The warming system 700 can be similar to warming system 400 except the pocket 704 has a different orientation and position. The warming system 700 can include a clinical garment 702 having a pocket 704. The pocket 704 can be mounted on the outer surface of the clinical garment 702. In at least one embodiment, the clinical garment 702 can have a longitudinal axis 706 that is oriented from the neck opening 722 to the hemline 724.

The pocket 704 can be oriented for a side opening. For example, the pocket axis 708 can follow the opening orientation of the flap portion 712. The pocket axis 708 is shown approximately 90 degrees from the longitudinal axis 706. In at least one embodiment, the pocket axis 708 is established by the tip 710 of the flap portion 712 and the pocket nadir 718. As shown, the length dimension 714, and width dimension 716 of a sheet of material 726 can be sealed or fastened to the clinical garment 702 and one of the width dimensions can be left open.

In use, the tip 710 can be releasably sealed to a portion of the sheet of material 224 such that a clinician 720 can open the flap portion 712 to remove a pneumatic convective device. In another embodiment, the tip 710 can be unsealed such that it can be pulled up by the clinician 720.

Figure 8:
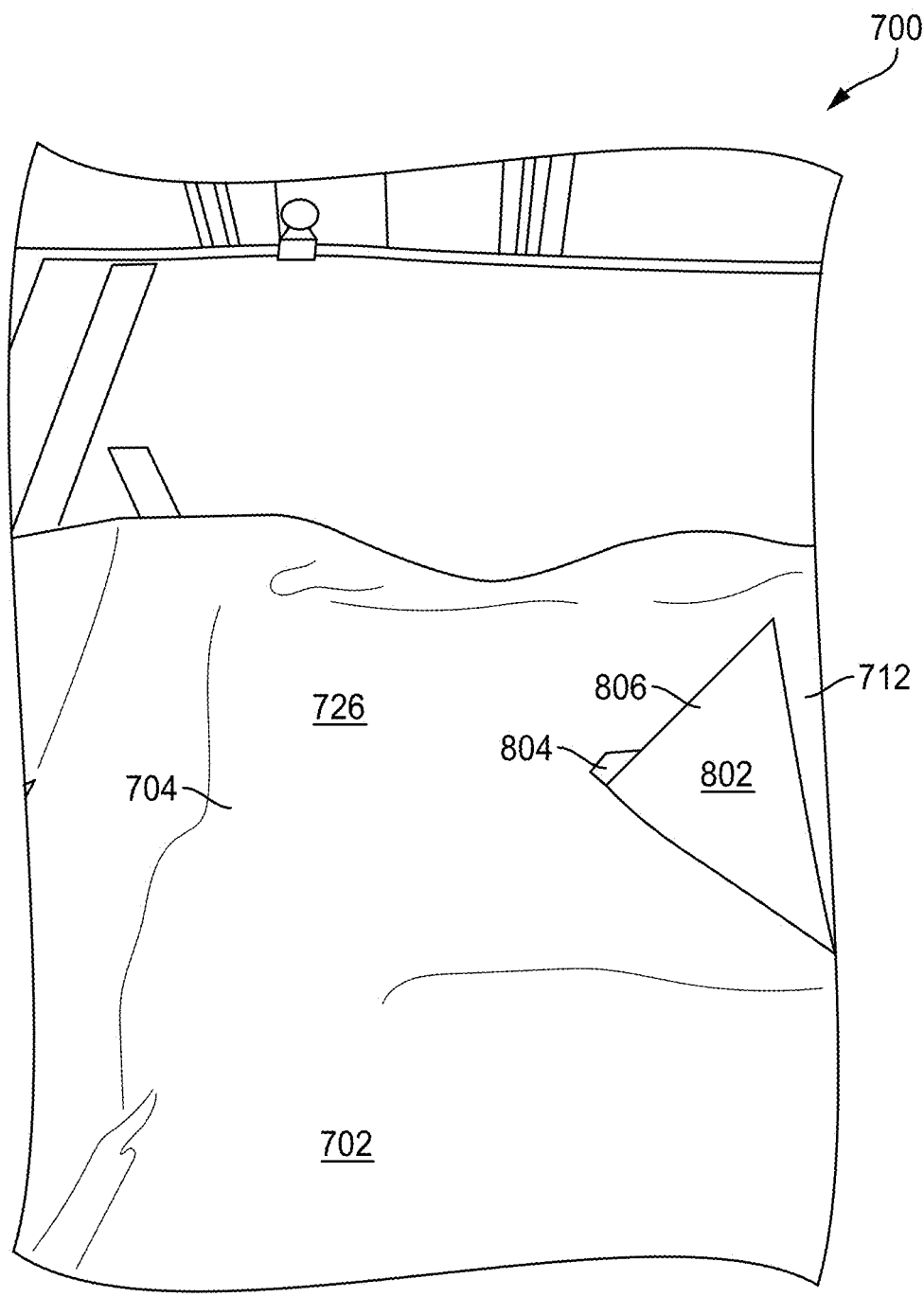
FIG. 8 illustrates the warming system 700 with the pocket in a second configuration in accordance with one embodiment.
Figure 9:
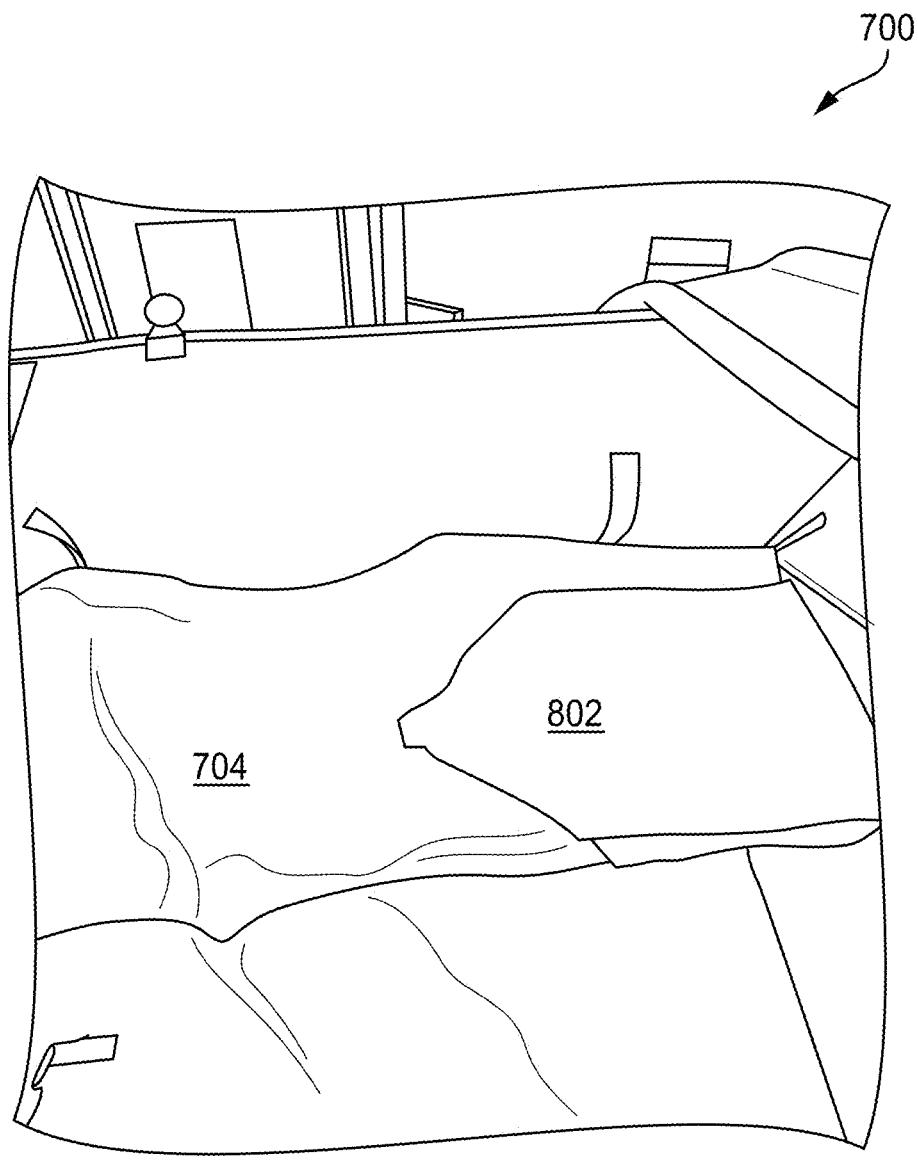
FIG. 9 illustrates the warming system 700 with a pneumatic convective device being removed from the pocket in accordance with one embodiment.

FIG. 8 illustrates an open pocket 704 with the flap portion 712 folded up to reveal a pocket opening 806 formed by the sheet of material 726. The sheet of material 726 of pocket 704 can have an indented region 804 to facilitate removal of the pneumatic convective device 802 from the pocket 704 as shown in FIG. 9. The pneumatic convective device 802 is shown in a partially-folded configuration.

FIGS. 19A-B illustrates a warming system 1900 similar to warming system 700 except that the pocket is formed from a portion of the clinical garment 1902 itself. For example, at least one fabric panel of the clinical garment 1902 can be folded over to create a pocket 1904 therein. The top edge 1906 of the panel can be attached permanently or detachably to the shoulder of the clinical garment 1902 to form the pocket 1904 therein. This pocket 1904 is shown as having openings 1908 on both sides and is closed on two sides. The pocket 1904 is aligned with the sleeves 1912 meaning that at least an axis running through both sleeves orthogonal to the longitudinal dimension (e.g., along longitudinal axis like in 706) of the gown also intersects the pocket 1904. In at least one embodiment, the pocket axis of the pocket 1904 can be similar to the pocket axis 708 in that it is oriented across the chest and along the sleeves 1912. The pocket 1904 can be configured to retain a pneumatic convective device 1910. In at least one embodiment, the volume (or internal surface area) of the pocket 1904 can be at least 1.5, 1.9, 2.0, 2.1, 2.2, or 2.3 times the volume (of internal surface area) of the folded pneumatic convective device 1910. In another embodiment, an opening of the pocket 1904 can be at least 1.0, 1.2, 1.3, 1.4, or 1.5 times the smallest cross sectional area of the folded pneumatic convective device 1910.

Figure 10:
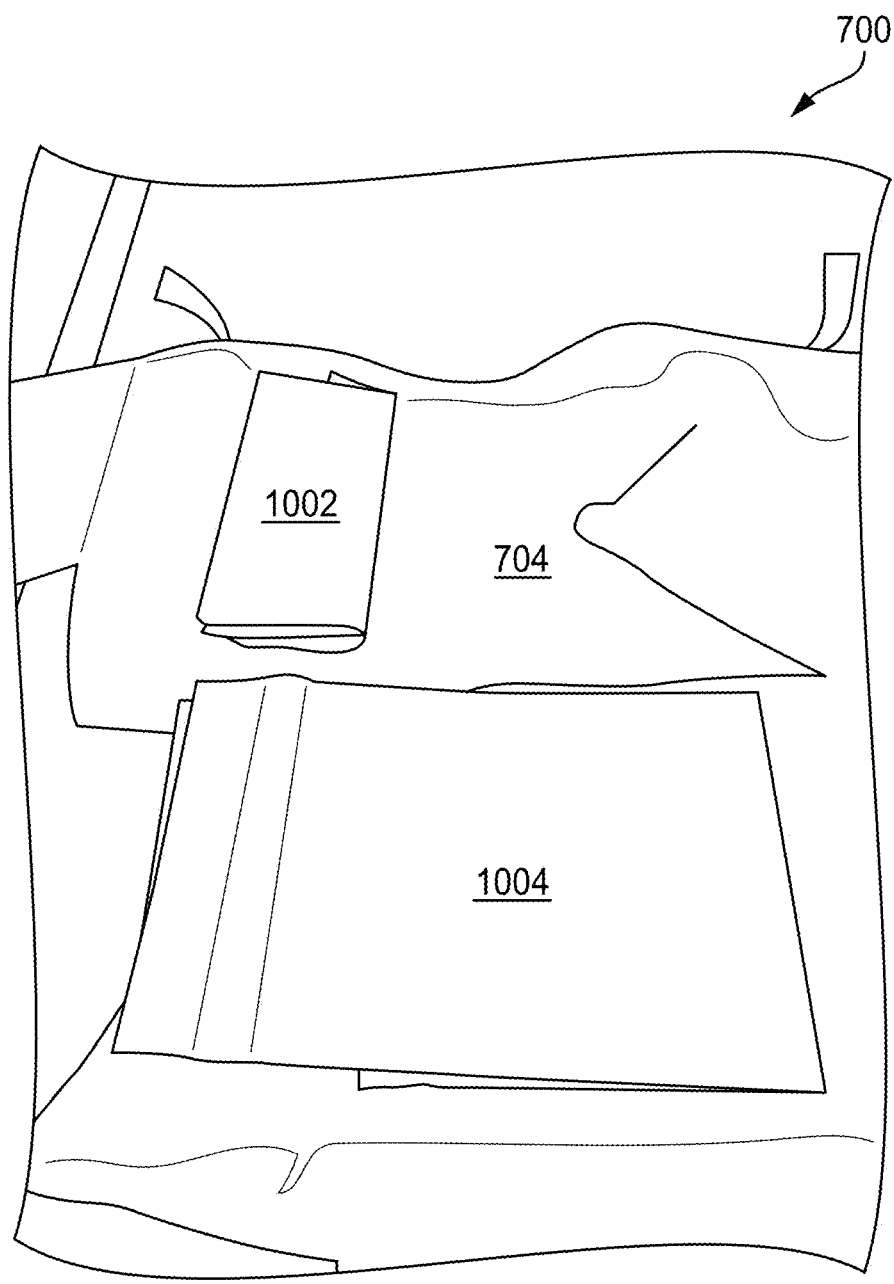
FIG. 10 illustrates the warming system 700 with two pneumatic convective devices in accordance with one embodiment.
Figure 11:
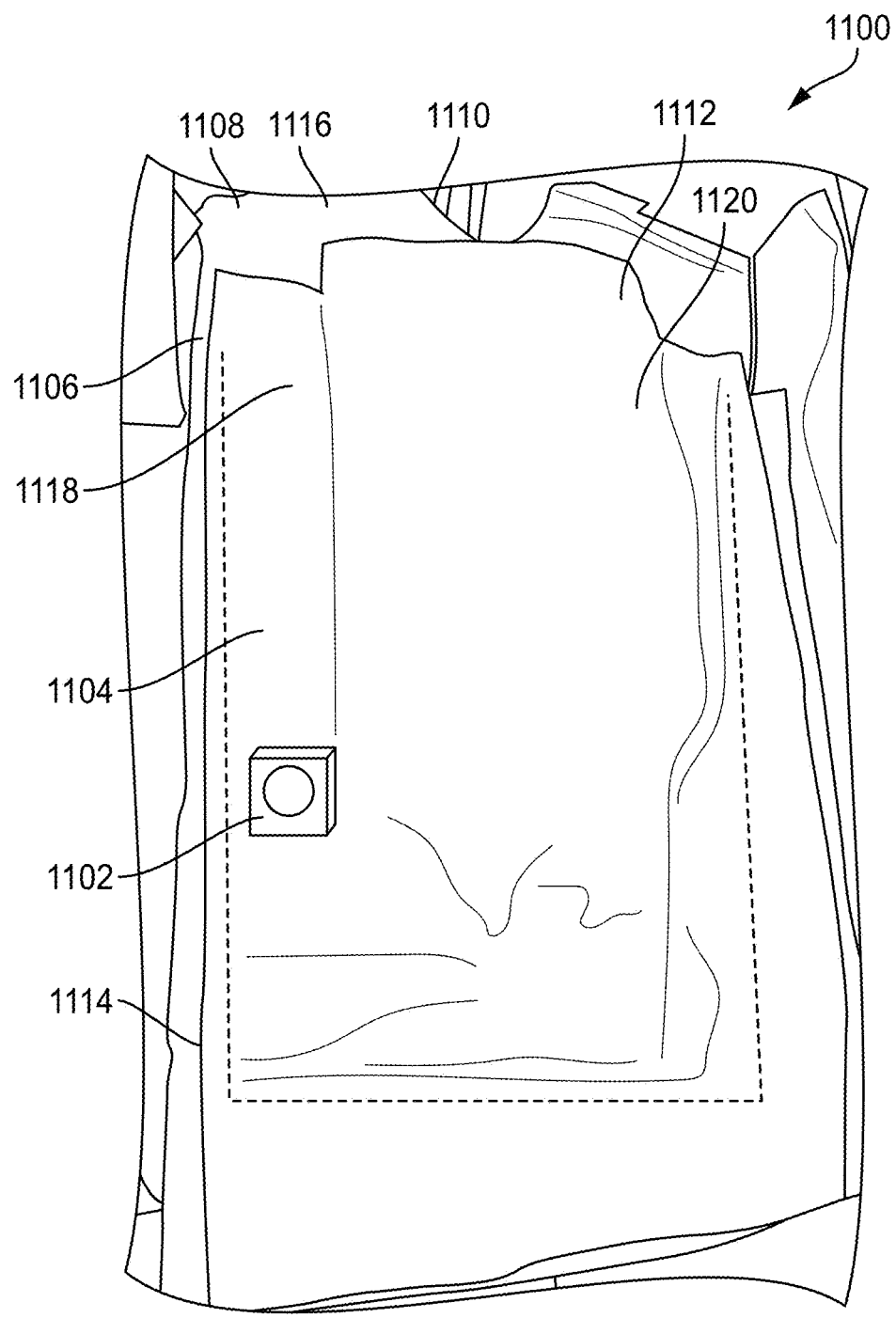
FIG. 11 illustrates an inner surface view of a warming system 1100 in accordance with one embodiment.

FIG. 10 illustrates the warming system 700 with two pneumatic convective devices. One pneumatic convective device is in a fully-folded configuration 1002 and the other pneumatic convective device is in a partially-folded configuration 1004. FIG. 10 illustrates the size difference between the two folding patterns and are used for illustration. In at least one embodiment, one or both pneumatic convective devices can be disposed in the pocket 704.

The fully-folded configuration 1002 can be formed by folding the pneumatic convective device at least 3 times, or at least 4 times which may form at least 3 or at least 4-fold creases. In at least one embodiment, the fully-folded configuration can result in a folded face of one of the folded sections of the pneumatic convective device. The folded face can have a first surface area and the entire pneumatic convective device can have a second surface area. The first surface area is no greater than 20% than the second surface area. In at least one embodiment, the fully-folded configuration can result in a thickness that is at least four times, or at least five times the thickness of an unfolded pneumatic convective device (as measured from a side-cross section in a flaccid state). In at least one embodiment, the thickness of the fully-folded configuration can be no greater than 2 inches, no greater than 1 inch, no greater than 0.5 inches.

The thickness of the partially-folded configuration can be no greater than 1 inch, no greater than 0.5 inches, or no greater than 0.3 inches. The thickness of the partially-folded configuration can be half of the thickness of the fully-folded configuration.

The partially-folded configuration can be formed by folding the pneumatic convective device at least 1 time. In at least one embodiment, the partially-folded configuration can result in a folded face of one of the folded sections of the pneumatic convective device having a first surface area that is at least 40% of the second surface area of the pneumatic convective device. In at least one embodiment, the partially-folded configuration can result in a thickness that is at least two or at least three times the thickness of an unfolded pneumatic convective device (as measured from a side-cross section in a flaccid state).

FIG. 11-FIG. 16 illustrate a warming system 1100. The warming system 1100 can have a clinical garment 1108 with a pocket formed from a pneumatic convective device 1104 on an inner side (i.e., patient facing).

In at least one embodiment, the clinical garment 1108 can have an optional insulative material 1106 attached thereon. As shown, the insulative material 1106 is fixedly attached to the inner surface 1116 of the clinical garment 1108. The clinical garment 1108 can also have a neck opening 1110 for a patient's neck. In at least one embodiment, a portion of the neck opening 1110 is configured to contact the collarbone of a patient.

The clinical garment 1108 can also have a pneumatic convective device 1104 disposed thereon. As shown, the pneumatic convective device 1104 is permanently or releasably attached to the inner surface 1116. For example, a perimeter seal 1114 can bond a portion of the pneumatic convective device 1104 on three sides (except for a pocket opening 1118) to the optional insulative material 1106 and the clinical garment 1108. A pocket 1120 can be formed from the bonded three sides between the pneumatic convective device 1104 and the clinical garment 1108 and an unbound pocket opening 1118 formed from an edge of pneumatic convective device 1104 and a portion of the insulative material 1106 or clinical garment 1108. The pneumatic convective device 1104 can have an inlet 1102 for receiving warmed air from a convective warming unit.

A pneumatic convective device 1112 can be placed in the pocket opening 1118 such that it can be easily removed. In at least one embodiment, pneumatic convective device 1112 is not secured to the clinical garment 1108. The pneumatic convective device 1112 can be either in a fully-folded configuration or a partially-folded configuration but is shown in the partially-folded configuration.

Figure 12:
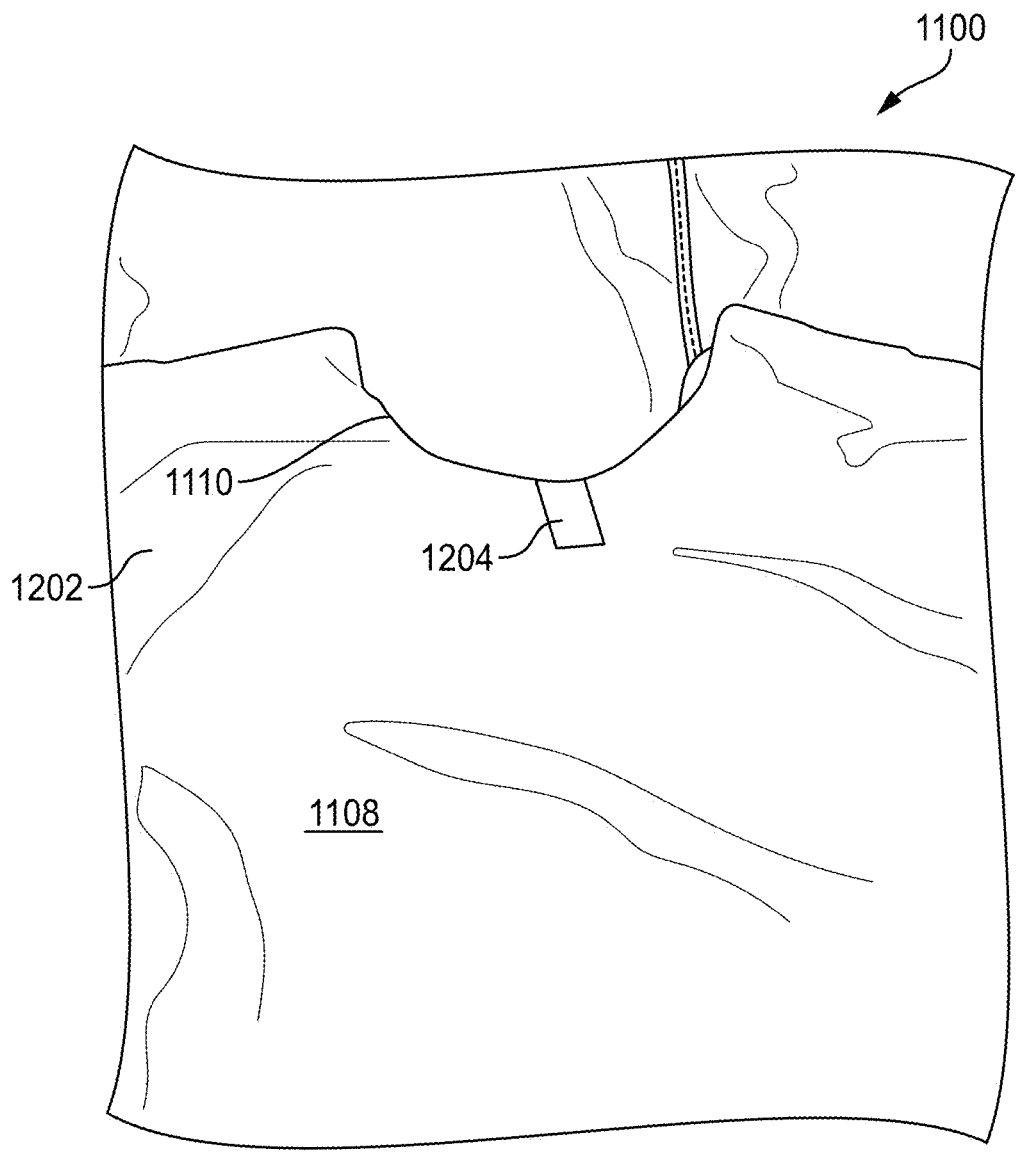
FIG. 12 illustrates an outer surface view of the warming system 1100 in accordance with one embodiment.

FIG. 12 illustrates the outer surface 1202 of the clinical garment 1108. From the outer surface 1202, a tab element 1204 can be visible. The tab element 1204 can be configured to attach to the pneumatic convective device 1112 and facilitate removal of the pneumatic convective device 1112 from the pocket 1120. The tab element 1204 is shown in the folded down position over a neck opening 1110 and releasably attached to the outer surface of the clinical garment to remain out of the way during wear by a patient.

Figure 13:
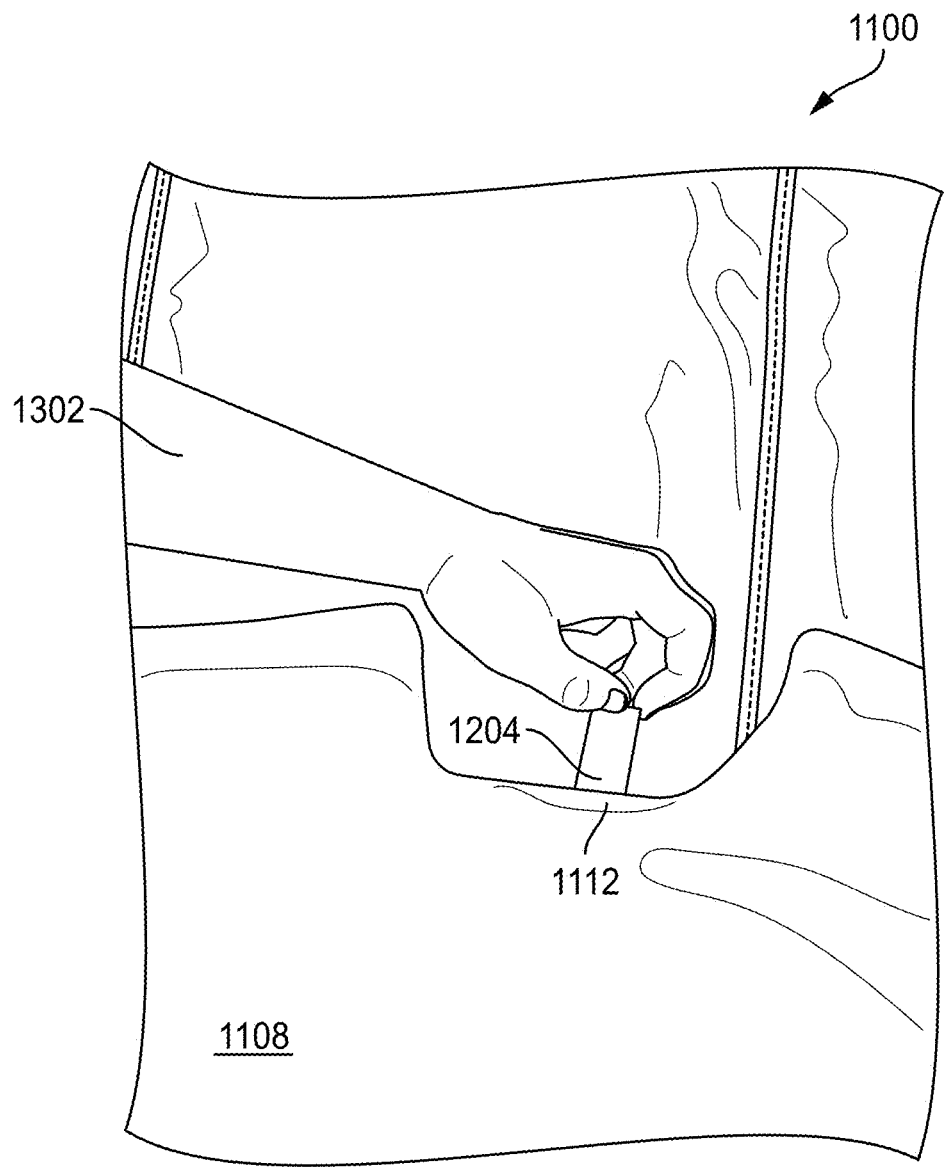
FIG. 13 illustrates the outer surface view of the warming system 1100 in accordance with one embodiment.

FIG. 13 illustrates a clinician 1302 applying a pulling force to the tab element 1204. The pulling force can be sufficient to remove the pneumatic convective device 1112 gradually and from the neck opening 1110.

Figure 14:
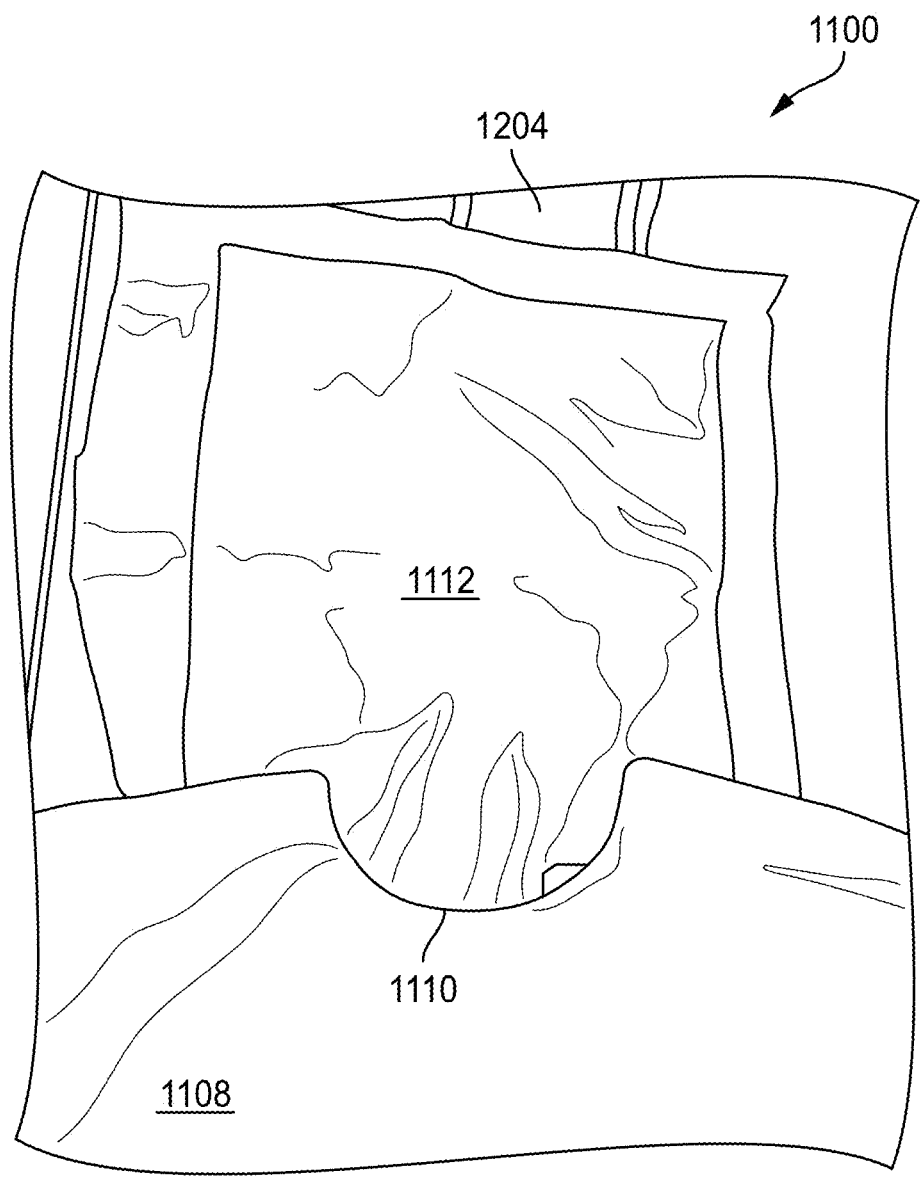
FIG. 14 illustrates the warming system 1100 in accordance with one embodiment.

FIG. 14 illustrates the pneumatic convective device 1112 being pulled from a first position to a second position beyond the neck opening 1110.

Figure 15:
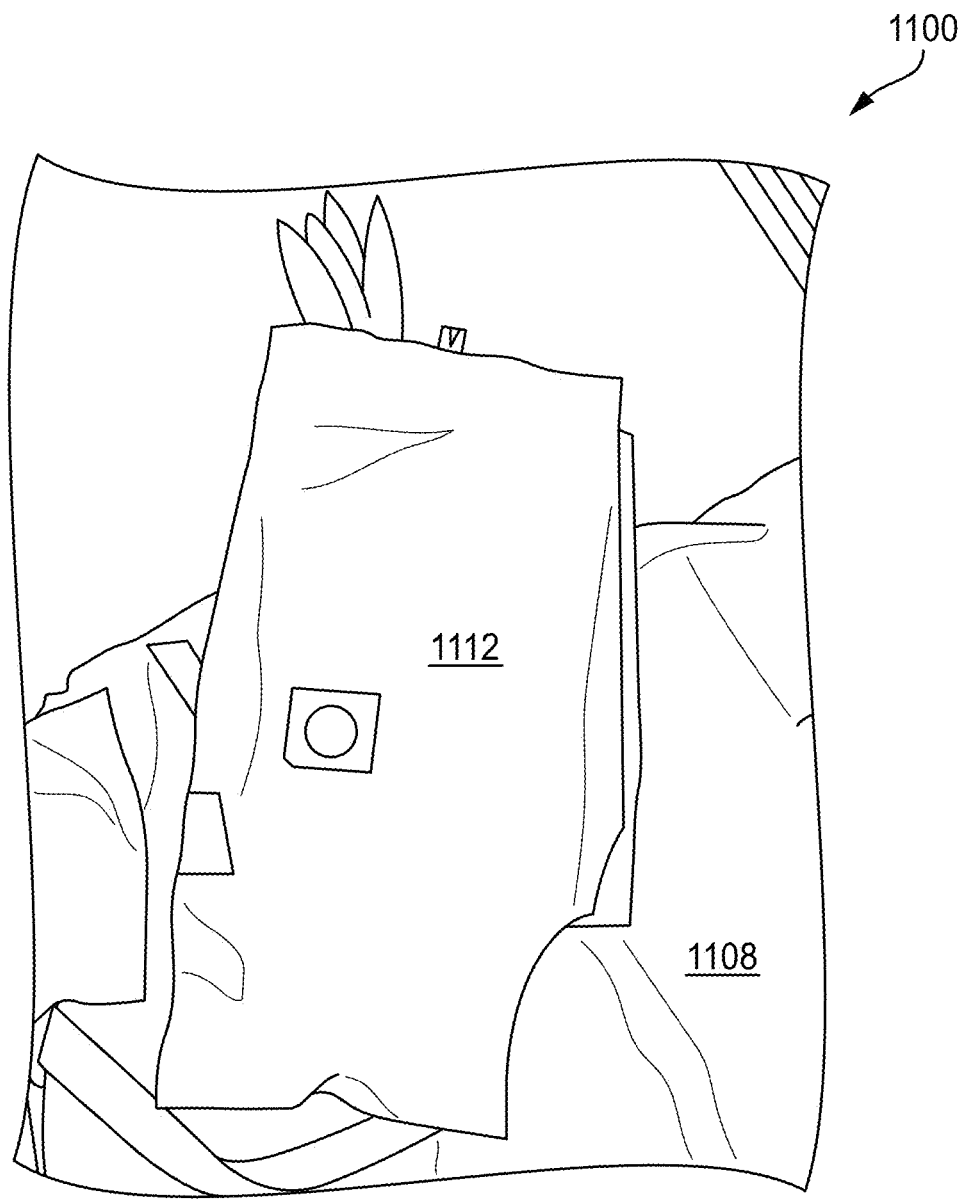
FIG. 15 illustrates the warming system 1100 with a pneumatic convective device removed from a pocket in accordance with one embodiment.

FIG. 15 illustrates the pneumatic convective device 1112 in a partially-folded configuration and being completely removed from the pocket 1120.

Figure 16:
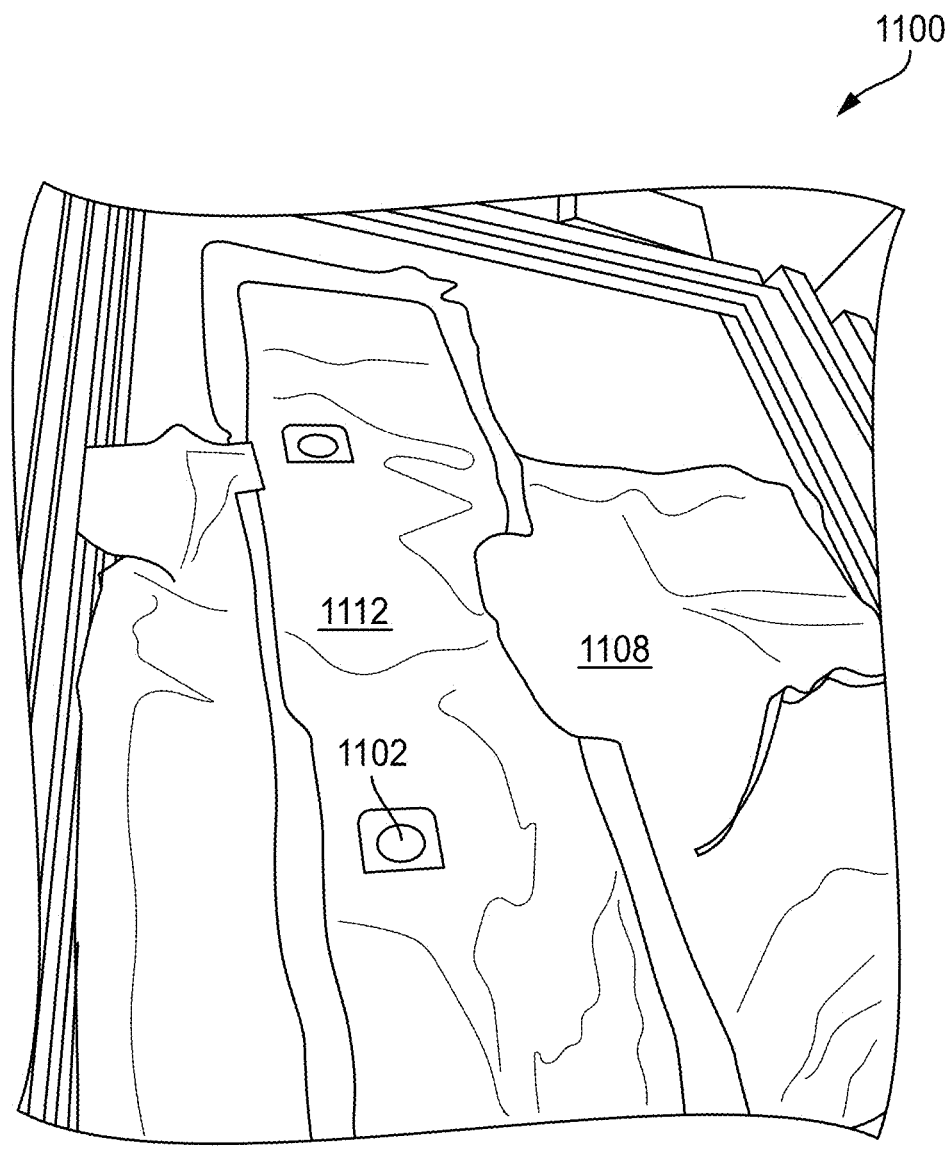
FIG. 16 illustrates the warming system 1100 with the pneumatic convective device deployed in accordance with one embodiment.

FIG. 16 illustrates the pneumatic convective device 1112 in a deployed configuration. The pneumatic convective device 1112 can be used by the clinician 1302 during a surgical procedure and the clinical garment 1108 can be removed for later use.

Figure 17:
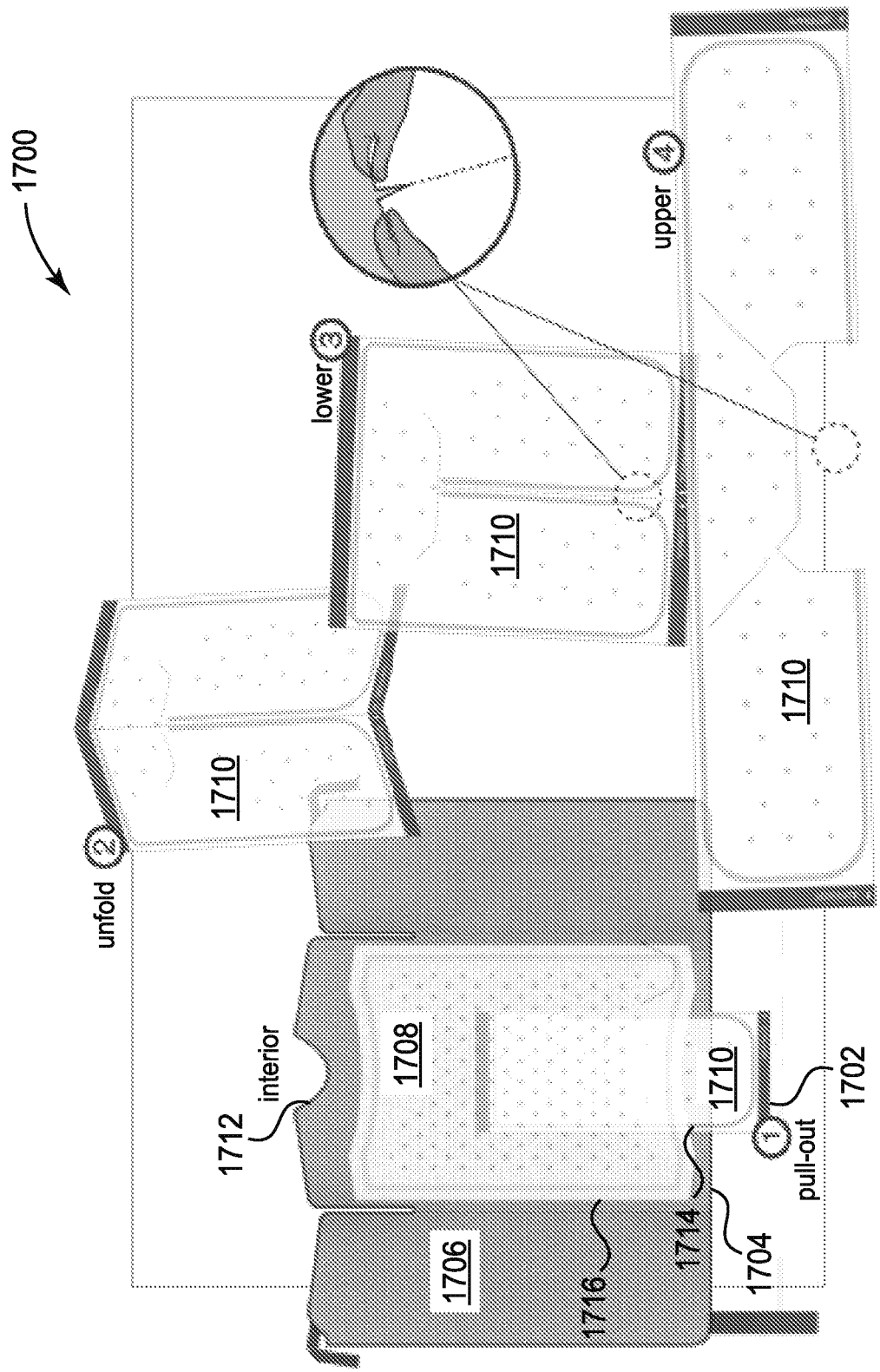
FIG. 17 illustrates a warming system 1700 in accordance with one embodiment.

FIG. 17 illustrates a warming system 1700 that is similar to warming system 1100 except that the pocket opening 1714 opens from the bottom portion of the clinical garment 1706. The clinical garment 1706 has a neck opening 1712 and a hemline 1704 opposite the neck opening 1712. The clinical garment 1706 can have a pneumatic convective device 1708 fixedly attached thereon along a perimeter seal 1716. The perimeter seal 1716 can leave at least one region near the hemline 1704 that is unsealed. The unsealed region can form a pocket opening 1714 dimensioned to receive a pneumatic convective device 1710. The pneumatic convective device 1710 can have an integral tab element 1702. In at least one embodiment, the pneumatic convective device 1710 is in a partially-folded configuration. In at least one embodiment, the pneumatic convective device 1710 can be a lithotomy-style blanket sold by 3M. For example, the pneumatic convective device 1710 can transition between an upper-body-style blanket and a lithotomy-style blanket.

Figure 18:
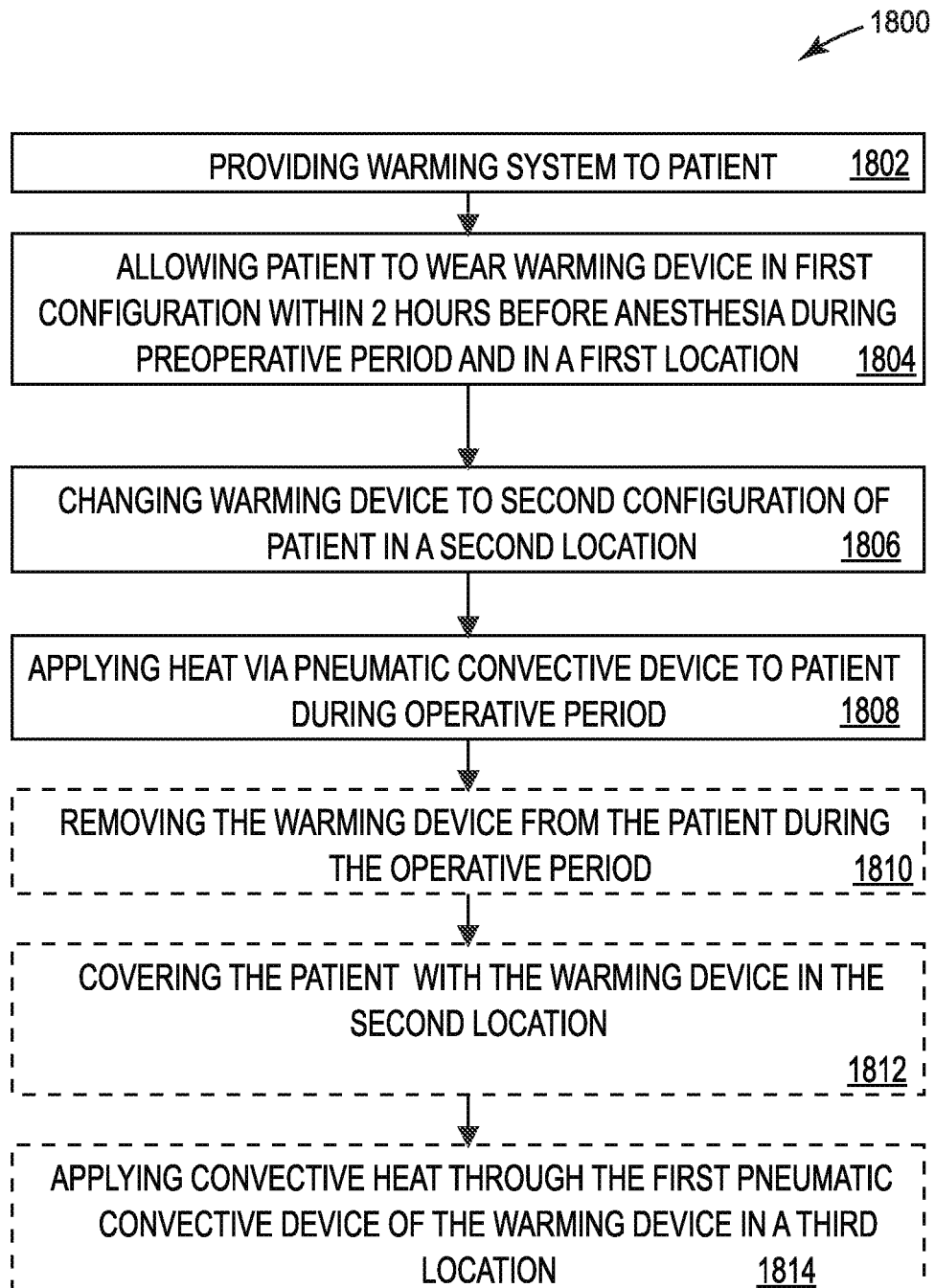
FIG. 18 illustrates a routine in accordance with one embodiment.

FIG. 18 illustrates a flowchart of a method 1800 of applying therapeutic warming to a patient.

The method 1800 can begin at block 1802. In block 1802, the warming system described herein can be provided to the patient. A manufacturer can provide one or more of the components of the warming system to the clinician who can further provide it to the patient according to the instructions of the manufacturer. In block 1804, the clinician can allow the patient to wear the warming device that can include at least a first pneumatic convective device. The patient can wear the warming device during a preoperative period of a perioperative period. For example, the patient can preferably wear the warming device within 2 hours, within 1 hour, or within 30 minutes before anesthesia.

The warming device can help to pre-warm the patient before the anesthesia sufficient to maintain normothermia during anesthesia. Optionally, block 1804 can also include applying heat to the patient via a first pneumatic convective device that is fixedly attached to the warming device. The clinician can activate an active convective heat modality for the warming device. The heat application during block 1804 can result in pre-warming prior to anesthesia. In at least one embodiment, the warming device can contain a passive modality for pre-warming the patient and reducing heat losses. For example, the warming device can also have an insulative material that can reduce heat loss by the patient.

In at least one embodiment, the clinician can place the warming device onto the patient in a first location. For example, the first location can be dependent on hospital configurations, but the first location can be a separate surgical waiting area, a patient recovery room, or preoperative bay. Preferably, the first location can have a power outlet.

In block 1806, the clinician can change the warming device from a first configuration to a second configuration before anesthesia in a second location. In at least one embodiment, the second location is an operating theatre, or operating room where the surgery is taking place. In at least one embodiment, the first location and the second location are the same. For example, pre-warming of the second configuration can be related to a feature of the warming device. For example, the second configuration can be an opened pocket, a removable pneumatic convective device, or a deployment of a pneumatic convective device. The changing to the second configuration can also occur during the operative period of the perioperative period. In at least one embodiment, the operative period can begin within 10 minutes, or within 5 minutes before anesthesia is delivered and continue while the patient is anesthetized.

In at least one embodiment, the changing of the warming device configurations can occur at least 5 minutes before, at least 10 minutes before the start of anesthesia. In another embodiment, the changing can occur during anesthesia of the patient.

In block 1808, the clinician can apply heat to the patient during the operative period. The total amount of heat is dependent on the clinician preferences; however, the convective warming unit can be capable to output at least 300 watts, at least 350 watts, or at least 400 watts at a hose end. In at least one embodiment, the power consumption of the convective warming unit can be at least 1400 watts. The heat applied can be sufficient to maintain normothermia of a patient. In at least one embodiment, the heat can be applied through the warming device or from a separate pneumatic convective device that is attached thereon. The temperature at the hose-end, prior to the air entering the pneumatic convective device, may range from ambient to up to 46° C., but preferably at least 37 degrees C. The airflow at the hose-end, prior to the air entering the pneumatic convective device, may be between 5-15 CFM, at least 20 CFM, at least 30 CFM, or even 30-50 CFM. The pressure inside the pneumatic convective device may range of 0.05 to 1.2 inches $H_2O$.

Block 1810 to block 1814 can be optional. In block 1810, the clinician can remove the warming device from the patient during the operative period. For example, during a surgical procedure, the warming device can interfere with some surgical procedures (such as an abdominal incision). Thus, to provide warming, the warming device can be removed to expose a surgical treatment area, and optionally apply the heat via a separate pneumatic convective device that is part of the warming system. The warming device can be set aside for later use.

In block 1812, the clinician can retrieve the warming device and cover the patient with the warming device. For example, after the surgical procedure is over, but while the patient is anesthetized, the clinician can cover the patient for modesty in the second location. After the patient is covered, then the patient can be transported to a third location. The third location can be a post-operative recovery bay (i.e., PACU) or a patient room. In at least one embodiment, the separate pneumatic convective device can be discarded.

In block 1814, the clinician can apply heat to the patient through the first pneumatic convective device attached to the warming device. The heat can be such that the patient is comfort warmed during the post-operative period of the perioperative period. The post-operative period can generally be in the third location. In at least one embodiment, the heat can be for comfort warming during block 1814. For example, the heat can be no greater than 500 watts, no greater than 400 watts, or no greater than 200 watts.

List of Illustrative Embodiments

1. A warming system (or kit), comprising:
    a warming device, comprising:
        a clinical garment comprising a body portion adapted to cover a portion of a patient, an inner surface for facing the patient, and an outer surface for facing away from the patient, wherein the body portion includes sleeves sized and positioned for receiving the patient's arms, wherein the body portion includes a torso portion adapted to cover an anterior torso of a patient;
        a first pneumatic convective device disposed adjacent to the inner surface; and
        an opening formed in the clinical garment for admitting a stream of pressurized, warmed air into the first pneumatic convective device; and
    a second pneumatic convective device in a fully-folded configuration or partially-folded configuration and disposed within a portion of the clinical garment.
2. The warming system (or kit) of embodiment 1, wherein the second pneumatic convective device is disposed on the outer surface.

3. The warming system (or kit) of embodiment 2, wherein the second pneumatic convective device is releasably attached to the outer surface of the warming device on the torso portion.

4. The warming system (or kit) of any of the preceding embodiments, wherein a portion of the second pneumatic convective device is releasably attached to the clinical garment along a longitudinal axis.

5. The warming system (or kit) of any of the preceding embodiments, further comprising a convective warming unit configured to provide the stream of pressurized, warmed air to the opening having a heat transfer of at least 300 watts.

6. The warming system (or kit) of any of the preceding embodiments, wherein the body portion further includes a neck opening and a hemline, a rear slit extending from the neck opening to a hemline and fastening devices near the rear slit for attaching opposing sides of the rear slit, a longitudinal axis extends from the neck opening to the hemline.

7. The warming system (or kit) of any of the preceding embodiments, wherein the second pneumatic convective device is in a sealed package.

8. The warming system (or kit) of embodiment 7, wherein the sealed package has a volume of no greater than 40 cubic inches when the second pneumatic convective device is in a fully-folded configuration.

9. The warming system (or kit) of any of the preceding embodiments, wherein a thickness of the fully-folded configuration is no greater than 1 inch and a thickness of partially-folded configuration is no greater than 0.5 inch.

10. The warming system (or kit) of any of the preceding embodiments, wherein the warming device comprises a pocket.

11. The warming system (or kit) of embodiment 10, wherein the pocket is dimensioned to receive the sealed package.

12. The warming system (or kit) of any of the preceding embodiments, wherein the warming device comprises a pocket dimensioned to receive a portion of the second pneumatic convective device without head space.

13. The warming system (or kit) of embodiment 12, wherein the pocket has a pocket opening that has an openable circumference of at least 15 inches.

14. The warming system (or kit) of embodiment 13, wherein the pocket opening has at least one dimension that is at least 7 inches.

15. The warming system (or kit) of embodiment 12, wherein the pocket is internal to the clinical garment and accessible via the outer surface.

16. The warming system (or kit) of embodiment 15, wherein the outer surface has a pocket opening that is dimensioned to receive the second pneumatic convective device in a fully-folded configuration or a partially-folded configuration.

17. The warming system (or kit) of embodiment 12, wherein the pocket comprises a first sheet of material having a first pocket end, a second pocket end and a side portion, wherein the first sheet of material is attached to the clinical garment at the second pocket end and the side portion.

18. The warming system (or kit) of embodiment 17, wherein the first pocket end comprises an indented region.

19. The warming system (or kit) of embodiment 17, wherein the first sheet of material is fastened to the clinical garment along a fastened region of the first sheet of material using a fastening device.

20. The warming system (or kit) of embodiment 19, wherein the fastening device is a fixed fastener.

21. The warming system (or kit) of embodiment 19, wherein the fastened region is continuous along a perimeter of the first sheet of material.

22. The warming system (or kit) of embodiment 19, wherein the first sheet of material has a line of weakness disposed proximate to the first pocket end.

23. The warming system (or kit) of embodiment 17, wherein the first sheet of material is unattached or releasably attached to the clinical garment at the first pocket end to form a pocket opening.

24. The warming system (or kit) of embodiment 17, wherein the pocket comprises a second sheet of material forming a flap over a portion of the first sheet of material, the second sheet of material having a first flap end and a second flap end, the first flap end is attached proximate the first pocket end and is releasably attached to the first sheet of material.

25. The warming system (or kit) of embodiment 24, wherein the second flap end comprises a tip that is configured to engage the first sheet of material.

26. The warming system (or kit) of embodiment 17, wherein the first pocket end and the second pocket end form a pocket axis, wherein an angle formed between the pocket axis and the longitudinal axis is less than 90 degrees.

27. The warming system (or kit) of embodiment 17, wherein the first pocket end is oriented toward a neck opening.

28. The warming system (or kit) of embodiment 17, wherein the pocket is located within 10 inches of a portion of the neck opening.

29. The warming system (or kit) of embodiment 12, wherein a portion of the pocket intersects the longitudinal axis.

30. The warming system (or kit) of any of the preceding embodiments, wherein the warming device further comprises an insulative material, wherein the insulative material has an R-value of between 1.5 and 3 R, inclusive.

31. The warming system (or kit) of embodiment 30, wherein the clinical garment has a first side and a second side, the first side has a first garment surface area, that includes the body portion and the sleeves, the insulative material has a second surface area, the second surface area is at least 15% of the first garment surface area.

32. The warming system (or kit) of any of the preceding embodiments, wherein the pocket is formed on an inner side of the warming device.

32a. The warming system (or kit) of any of the preceding embodiments, wherein the pocket is formed from a portion of the clinical garment.

32b. The warming system (or kit) of any of the preceding embodiments, wherein the pocket has two openings.

32c. The warming system (or kit) of any of the preceding embodiments, wherein the pocket is proximate to the sleeves of the clinical garment.

32d. The warming system (or kit) of any of the preceding embodiments, wherein the pocket is aligned with the sleeves of the clinical garment.

33. The warming system (or kit) of any of the preceding embodiments, wherein the first pneumatic convective device is fixedly attached to the clinical garment or portion thereof along a perimeter seal to form the pocket.

34. The warming system (or kit) of any of the preceding embodiments, wherein the perimeter seal is adjacent to an edge of the first pneumatic convective device.

35. The warming system (or kit) of embodiment 34, wherein the first pneumatic convective device is not attached proximate the neck opening to form a pocket opening between the clinical garment or insulative material and an edge of the first pneumatic convective device.

36. The warming system (or kit) of embodiment 35, wherein the second pneumatic convective device comprises a tab element accessible on the outer surface of the clinical garment.

37. The warming system (or kit) of embodiment 30, wherein the warming device has a warming device weight and the second pneumatic convective device has a pneumatic convective device weight, the pneumatic convective device weight is no greater than 50 percent of the warming device weight.

38. The warming system (or kit) of embodiment 30, wherein the insulative material is disposed on the inner surface of the clinical garment.

39. The warming system (or kit) of any of the preceding embodiments, wherein one of the sleeves has a slit, and a recloseable fastener configured to releasably attach opposing sides of the slit.

40. The warming system (or kit) of embodiment 39, wherein the recloseable fastener selected from the group consisting of buttons, string, snaps, repositionable adhesive, hook and eye elements, double-sided adhesive, hook and loop elements, and rivets.

41. The warming system (or kit) of any of the preceding embodiments, wherein the clinical garment comprises a non-woven material.

42. The warming system (or kit) of any of the preceding embodiments, wherein the clinical garment is formed from an insulative material.

43. The warming system (or kit) of any of the preceding embodiments, further comprising a patient, wherein the pocket is positioned on an upper half of the transverse plane of the patient.

44. A method comprising:
providing the warming system (or kit) of embodiment 1 to embodiment 43 to a patient;
allowing the patient to wear the warming device in a first configuration within 2 hours before anesthesia during a preoperative period and in a first location;
changing the warming device to a second configuration at least 10 minutes before, at least 5 minutes before, or during anesthesia of a patient at a second location;
applying heat via a pneumatic convective device to the patient during an operative period.

45. The method of embodiment 44, wherein the first configuration of the warming device comprises a first pneumatic convective device fixedly attached to the clinical garment and a pocket with the second pneumatic convective device contained therein; and
the method further comprises applying heat to the patient through the first pneumatic convective device via the convective warming unit for at least 10 minutes.

46. The method of embodiment 45, wherein changing the warming device comprises removing the second pneumatic convective device from the pocket of the warming device, wherein the second configuration of the warming device comprises no second pneumatic convective device in the pocket;
wherein the pneumatic convective device is the second pneumatic convective device.

47. The method of embodiment 44, further comprising:
removing the warming device from the patient during the operative period.

48. The method of embodiment 47, further comprising:
covering the patient with the warming device in the second location; and
applying convective heat through the first pneumatic convective device of the warming device in a third location.

What is claimed is:

1. A warming system, comprising:
a warming device, comprising:
a clinical garment comprising a body portion adapted to cover a portion of a patient, an inner surface for facing the patient, and an outer surface for facing away from the patient, wherein the body portion includes sleeves sized and positioned for receiving the patient's arms, wherein the body portion includes a torso portion adapted to cover an anterior torso of a patient;
a first pneumatic convective device disposed adjacent to the inner surface; and
an opening formed in the clinical garment for admitting a stream of pressurized, warmed air into the first pneumatic convective device; and
a second pneumatic convective device in a fully-folded configuration or partially-folded configuration and disposed on a portion of the clinical garment, wherein the second pneumatic convective device is disposed on the outer surface.

2. The warming system of claim 1, wherein the second pneumatic convective device is releasably attached to the outer surface of the warming device on the torso portion.

3. The warming system of claim 1, further comprising a convective warming unit configured to provide the stream of pressurized, warmed air to the opening at a temperature of at least 37 degrees C. and an airflow of at least 20 cfm.

4. The warming system of claim 1, wherein the body portion further includes a neck opening and the hemline, a rear slit extending from the neck opening to a hemline and fastening devices near the rear slit for attaching opposing sides of the rear slit, a longitudinal axis extends from the neck opening to the hemline.

5. The warming system of claim 1, wherein a thickness of the fully-folded configuration is no greater than 1 inch and a thickness of partially-folded configuration is no greater than 0.5 inches.

6. The warming system of claim 1, wherein the warming device comprises a pocket dimensioned to receive the second pneumatic convective device.

7. The warming system of claim 6, wherein the pocket has a pocket opening that has an openable circumference of at least 15 inches.

8. The warming system of claim 6, wherein the pocket comprises a first sheet of material having a first pocket end, a second pocket end and a side portion, wherein the first sheet of material is attached to the clinical garment at the second pocket end and the side portion.

9. The warming system of claim 6, wherein the first pocket end comprises an indented region.

10. The warming system of claim 8, wherein the first sheet of material is fastened to the clinical garment along a fastened region of the first sheet of material using a fastening device, the fastening device is a fixed fastener, and the fastened region is continuous along a perimeter of the first sheet of material.

11. The warming system of claim 10, wherein the first sheet of material has a line of weakness disposed proximate to the first pocket end.

12. The warming system of claim 11, wherein the first sheet of material is unattached or releasably attached to the clinical garment at the first pocket end to form a pocket opening.

13. The warming system of claim 12, wherein the pocket comprises a second sheet of material forming a flap over a portion of the first sheet of material, the second sheet of material having a first flap end and a second flap end, the first flap end is attached proximate the first pocket end and is releasably attached to the first sheet of material.

14. The warming system of claim 1, wherein the warming device further comprises an insulative material, wherein the insulative material has an R-value of between 0.5 and 3 R, inclusive.

15. A warming system, comprising:
a warming device, comprising:
  a clinical garment comprising a body portion adapted to cover a portion of a patient, an inner surface for facing the patient, and an outer surface for facing away from the patient, wherein the body portion includes sleeves sized and positioned for receiving the patient's arms, wherein the body portion includes a torso portion adapted to cover an anterior torso of a patient;
  a first pneumatic convective device disposed adjacent to the inner surface, wherein a pocket is formed on an inner side of the warming device, the first pneumatic convective device is fixedly attached to the clinical garment or portion thereof along a perimeter seal to form the pocket; and
  an opening formed in the clinical garment for admitting a stream of pressurized, warmed air into the first pneumatic convective device; and
a second pneumatic convective device in a fully-folded configuration or partially-folded configuration and disposed on a portion of the clinical garment.

16. The warming system of claim 15, wherein the perimeter seal is adjacent to an edge of the first pneumatic convective device.

17. A method comprising:
providing the warming system of claim 1 to a patient;
allowing the patient to wear the warming device in a first configuration within 2 hours before anesthesia during a preoperative period and in a first location;
changing the warming device to a second configuration at least 5 minutes before or during anesthesia of a patient at a second location;
applying heat via at least one of the first or second pneumatic convective devices to the patient during an operative period.

18. The method of claim 17, wherein the first configuration of the warming device comprises the first pneumatic convective device fixedly attached to the clinical garment and a pocket with the second pneumatic convective device contained therein;
and the method further comprises applying heat to the patient through the first pneumatic convective device via a convective warming unit for at least 5 minutes.

19. The method of claim 18, wherein changing the warming device to the second configuration comprises removing the second pneumatic convective device from the pocket of the warming device, wherein the second configuration of the warming device comprises no second pneumatic convective device in the pocket.

* * * * *